United States Patent
Katz et al.

(10) Patent No.: US 8,835,170 B2
(45) Date of Patent: Sep. 16, 2014

(54) METHODS AND COMPOSITIONS USEFUL FOR DIABETIC WOUND HEALING

(75) Inventors: Adam J. Katz, Charlottesville, VA (US); Anna M. Parker, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 60 days.

(21) Appl. No.: 12/444,412

(22) PCT Filed: Oct. 5, 2007

(86) PCT No.: PCT/US2007/021432
§ 371 (c)(1),
(2), (4) Date: Jan. 7, 2010

(87) PCT Pub. No.: WO2008/060374
PCT Pub. Date: May 22, 2008

(65) Prior Publication Data
US 2010/0111897 A1    May 6, 2010

Related U.S. Application Data

(60) Provisional application No. 60/850,001, filed on Oct. 6, 2006.

(51) Int. Cl.
| | |
|---|---|
| C12N 5/00 | (2006.01) |
| C12N 5/02 | (2006.01) |
| C12N 5/08 | (2006.01) |
| C07K 1/00 | (2006.01) |
| C07K 14/00 | (2006.01) |
| A01N 63/00 | (2006.01) |
| A61K 35/28 | (2006.01) |
| A61K 38/18 | (2006.01) |
| A61K 38/19 | (2006.01) |

(52) U.S. Cl.
CPC .............. *A61K 35/28* (2013.01); *A61K 2300/00* (2013.01); *A61K 38/18* (2013.01); *A61K 38/19* (2013.01)
USPC ........... 435/373; 435/366; 435/371; 435/377; 424/93.3; 530/351

(58) Field of Classification Search
CPC ....... A61K 35/28; A61K 38/18; A61K 38/19; A61K 2300/00
USPC ................. 435/366, 371, 373, 377; 424/93.3; 530/351
See application file for complete search history.

(56) References Cited

U.S. PATENT DOCUMENTS

| | | |
|---|---|---|
| 5,286,716 A | 2/1994 | Risau et al. |
| 5,486,359 A | 1/1996 | Caplan et al. |
| 5,591,625 A | 1/1997 | Gerson et al. |
| 5,612,029 A | 3/1997 | Bennett et al. |
| 5,827,735 A | 10/1998 | Young et al. |
| 5,827,740 A | 10/1998 | Pittenger |
| 5,830,756 A | 11/1998 | Haskill et al. |
| 5,906,934 A | 5/1999 | Grande et al. |
| 5,908,784 A | 6/1999 | Johnstone et al. |
| 6,200,606 B1 | 3/2001 | Peterson et al. |
| 6,429,013 B1 | 8/2002 | Halvorsen et al. |
| 7,470,537 B2 | 12/2008 | Hedrick et al. |
| 7,514,075 B2 | 4/2009 | Hedrick et al. |
| 7,932,084 B2 | 4/2011 | Katz et al. |
| 8,592,209 B2 | 11/2013 | Khurgel |
| 2001/0033834 A1 | 10/2001 | Wilkison et al. |
| 2002/0076400 A1 | 6/2002 | Katz et al. |
| 2003/0153078 A1 | 8/2003 | Libera et al. |
| 2004/0210309 A1 | 10/2004 | Denzer et al. |
| 2006/0182724 A1 | 8/2006 | Riordan |
| 2007/0116676 A1 | 5/2007 | Kida et al. |
| 2010/0098739 A1 | 4/2010 | Katz et al. |
| 2010/0111897 A1 | 5/2010 | Katz et al. |

FOREIGN PATENT DOCUMENTS

| | | |
|---|---|---|
| AU | 2007320031 B2 | 5/2013 |
| JP | 2005502352 A | 1/2005 |
| JP | 2005114178 | 12/2005 |
| JP | 2009525044 A | 7/2009 |
| KR | 20050012208 | 1/2005 |
| WO | WO-0053795 A1 | 9/2000 |
| WO | WO-03022988 A2 | 3/2003 |
| WO | WO-03030957 A1 | 4/2003 |
| WO | WO-03084468 A2 | 10/2003 |

(Continued)

OTHER PUBLICATIONS

Miguel et al., 2006, US 20060045872 A1.*
Sayre et al., 2006, US 20060147430 A1.*
Libera et al., 2001, US Patent No. 7,887,843 B2.*
Khurgel et al., 2009, US 20090304643 A1, effective filing date, Jan. 30, 2006.*
Kang et al., 2007, US 20070110729 A1, effective filing date, Nov. 16, 2005.*
Wu et al., 2012, Aging Research reviews, vol. 11, p. 32-40.*
Steinert et al., 2007, Arthritis Research & therapy, vol. 9, No. 3, 213, p. 1-15.*

(Continued)

*Primary Examiner* — Shin Lin Chen
(74) *Attorney, Agent, or Firm* — Schwegman Lundberg & Woessner, P.A.

(57) ABSTRACT

The invention provides compositions and methods useful for treating wounds and enhancing wound healing, particularly for diabetic wound healing. One embodiment provides a method of treating a wound comprising administering to a subject in need thereof a therapeutically effective amount of adipose tissue derived stem cells to treat said wound, wherein the cells are cultured in the absence of serum prior to the administration to said subject. Another embodiment provides a method of treating a wound comprising administering to a subject in need thereof a therapeutically effective amount of adipose tissue derived stem cells to treat said wound, wherein the cells are cultured to induce the formation of at least one self-organizing mesenchymal blastema (SOMB) prior to the administration to said subject, wherein said SOMB is formed by culturing adipose tissue derived stem cells in hanging droplets.

9 Claims, 8 Drawing Sheets

(56) References Cited

FOREIGN PATENT DOCUMENTS

| WO | WO-03085099 A2 | 10/2003 |
|---|---|---|
| WO | WO-2004022988 | 3/2004 |
| WO | WO-2005045011 A1 | 5/2005 |
| WO | WO-2006014157 | 2/2006 |
| WO | WO-2006032054 A2 | 3/2006 |
| WO | WO-2006074075 | 7/2006 |
| WO | WO-2007019107 A2 | 2/2007 |
| WO | WO-2007030652 A2 | 3/2007 |
| WO | WO-2007030652 A3 | 3/2007 |
| WO | WO-2007089798 A1 | 8/2007 |
| WO | WO-2007089798 A2 | 8/2007 |
| WO | WO-2007089798 A3 | 8/2007 |
| WO | WO-2008060374 A2 | 5/2008 |
| WO | WO-2008060374 A3 | 5/2008 |
| WO | WO-2008064034 | 5/2008 |

OTHER PUBLICATIONS

Li et al., 2009, Transplant Immunology, vol. 21, p. 70-74.*
Sprangers et al., 2008, Kidney International, vol. 74, p. 14-21.*
Allegrucci et al., 2006, Human Reproduction Update, Vol. Advance Access published on Aug. 26, 2006, p. 1-18.*
Sato et al., 2003, Developmental Biology, vol. 260, p. 404-413.*
Abeyta et al., 2004, Human Molecular Genetics, vol. 13, No. 6, p. 601-608.*
Fraser et al., 2005, US 20050048034 A1.*
"U.S. Appl. No. 12/066,348, Ex Parte Quayle Office Action mailed Dec. 3, 2010", 5 pgs.
"U.S. Appl. No. 12/066,348, Non Final Office Action mailed Mar. 16, 2010", 8 pgs.
"U.S. Appl. No. 12/066,348, Notice of Allowance mailed Feb. 7, 2011", 4 pgs.
"U.S. Appl. No. 12/066,348, Response filed Nov. 25, 2009 to Restriction Requirement mailed Nov. 25, 2009", 3 pgs.
"U.S. Appl. No. 12/066,348, Response filed Sep. 16, 2010 to Non Final Office Action mailed Mar. 16, 2010", 10 pgs.
"U.S. Appl. No. 12/066,348, Restriction Requirement mailed Nov. 9, 2009", 7 pgs.
"U.S. Appl. No. 12/162,523, Non Final Office Action mailed Jul. 19, 2011", 12 pgs.
"U.S. Appl. No. 12/162,523, Preliminary Amendment mailed Jul. 29, 2008", 3 pgs.
"U.S. Appl. No. 12/162,523, Preliminary Amendment mailed Aug. 21, 2008", 3 pgs.
"U.S. Appl. No. 12/162,523, Response filed May 31, 2011 to Restriction Requirement mailed", 8 pgs.
"U.S. Appl. No. 12/162,523, Restriction Requirement mailed Apr. 29, 2011", 5 pgs.
"U.S. Appl. No. 12/580,419, Non Final Office Action mailed Sep. 1, 2011", 8 pgs.
"European Application Serial No. 07762669.5, Search Report mailed Apr. 14, 2009", 6 pgs.
"European Application Serial No. 07762669.5, Office Action mailed Apr. 21, 2010", 4 Pgs.
"European Application Serial No. 07762669.5, Office Action mailed Aug. 8, 2011", 5 pgs.
"European Application Serial No. 07762669.5, Office Action Response Filed Oct. 27, 2010", 59 pgs.
"International Application Serial No. PCT/US07/02572, International Search Report mailed Dec. 28, 2007", 4 pgs.
"International Application Serial No. PCT/US2006/034915, International Preliminary Report on Patentability mailed Mar. 10, 2009", 8 pgs.
"International Application Serial No. PCT/US2006/034915, Written Opinion mailed Mar. 19, 2008", 7 pgs.
"International Application Serial No. PCT/US2007/002572, International Preliminary Report on Patentability mailed Aug. 5, 2008", 9 pgs.
"International Application Serial No. PCT/US2007/002572, Written Opinion mailed Dec. 28, 2007", 8 pgs.
"International Application Serial No. PCT/US2007/021432, International Preliminary Report on Patentability mailed Apr. 7, 2009", 6 pgs.
"International Application Serial No. PCT/US2007/021432, Written Opinion mailed Sep. 12, 2008", 5 pgs.
Burris, T. P, et al., "A novel method for analysis of nuclear receptor function at natural promoters: peroxisome proliferator-activated receptor gamma agonist actions on aP2 gene expression detected using branched DNA messenger RNA quantitation.", Mol Endocrinol., 13(3), (Mar. 1999), 410-7.
Campos, L. S, "Neurospheres: insights into neural stem cell biology", J Neurosci Res., 78(6), (Dec. 15, 2004), 761-9.
Conley, B. J, et al., "Derivation, propagation and differentiation of human embryonic stem cells", Int J Biochem Cell Biol., 36(4), (Apr. 2004), 555-67.
Dontu, G., et al., "Survival of mammary stem cells in suspension culture: implications for stem cell biology and neoplasia.", J Mammary Gland Biol Neoplasia, 10(1), (Jan. 2005), 75-86.
Erickson, G. R., et al., "Chondrogenic Potential of Adipose Tissue-Derived Stromal Cells in Vitro and in Vivo", Biochem Biophys Res Commun., 290(2), (Jan. 18, 2002), 763-9.
Fuchs, E., et al., "Socializing with the neighbors: stem cells and their niche", Cell, 116(6), (Mar. 19, 2004), 769-78.
Gimble, J. M, et al., "The function of adipocytes in the bone marrow stroma", New Biol., 2(4), (Apr. 1990), 304-12.
Gorio, A., et al., "Fate of autologous dermal stem cells transplanted into the spinal cord after traumatic injury (TSCI).", Neuroscience, 125(1), (2004), 179-89.
Gronthos, S., et al., "Surface protein characterization of human adipose tissue-derived stromal cells", J Cell Physiol., 189(1), (Oct. 2001), 54-63.
Halvorsen, Y.-D. C., et al., "Extracellular Matrix Mineralization and Osteoblast Gene Expression by Human Adipose Tissue-Derived Stromal Cells", Tissue Engineering, 7(6), (2001), 729-741.
Halvorsen, Y.-D. C., et al., "Thiazolidinediones and Glucocorticoids Synergistically Induce Differentiation of Human Adipose Tissue Stromal Cells: Biochemical, Cellular, and Molecular Analysis", Metabolism, 50(4), (2001), 407-413.
Harp, J. B., et al., "Differential Expression of Signal Transducers and Activators of Transcription during Human Adipogenesis", Biochemical and Biophysical Research Communications, 281, (2001), 907-912.
Hauner, H., et al., "Promoting effect of glucocorticoids on the differentiation of human adipocyte precursor cells cultured in a chemically defined medium.", J Clin Invest., 84(5), (Nov. 1989), 1663-70.
Howson, K. M, et al., "The postnatal rat aorta contains pericyte progenitor cells that form spheroidal colonies in suspension culture", Am J Physiol Cell Physiol., 289(6), (Dec. 2005), C1396-C1407.
Huang, J I, et al., "Rat extramedullary adipose tissue as a source of osteochondrogenic progenitor cells", Plast Reconstr Surg. 109(3), (Mar. 2002), 1033-41.
Kindler, V., "Postnatal stem cell survival: does the niche, a rare harbor where to resist the ebb tide of differentiation, also provide lineage-specific instructions?", J Leukoc Biol., 78(4), (Oct. 2005), 836-44.
Kruse, C., et al., "Pluripotency of adult stem cells derived from human and rat pancreas", Applied Physics A, 79, (2004), 1617-1624.
Ogawa, Rei, "Chondrogenic and Osteogenic Differentiation of Adipose-derived Stem Cells Isolated from GFP Transgenic Mice.", J Nippon Med Sch 71(4), (2004), 240-241.
Oshima, Y, et al., "Fate of transplanted bone-marrow-derived mesenchymal cells during osteochondral repair using transgenic rats to simulate autologous transplantation.", Osteoarthritis Cartilage, 12(10), (Oct. 2004), 811-7 Pgs.
Oshima, Y., et al., "Behavior of transplanted bone marrow-derived GFP mesenchymal cells in osteochondral defect as a simulation of autologous transplantation.", J Histochem Cytochem., 53(2), (Feb. 2005), 207-216.
Rodbell, M., "Metabolism of isolated fat cells. II. The similar effects of phospholipase C (*Clostridium perfringens* alpha toxin) and of insulin on glucose and amino acid metabolism", J Biol Chem., 241(1), (Jan. 10, 1966), 130-9.

(56) References Cited

OTHER PUBLICATIONS

Rodriguez, A M, et al., "Adipocyte differentiation of multipotent cells established from human adipose tissue", Biochem Biophys Res Commun. 315(2), (Mar. 2004), 255-63.
Saladin, R., et al., "Differential Regulation of Peroxisome Proliferator Activated Receptor y1 (PPARy1) and PPARy2 Messenger RNA Expression in the Early Stages of Adipogenesis", Cell Growth & Differentiation, 10, (1999), 43-48.
Sen, A., et al., "Adipogenic Potential of Human Adipose Derived Stromal Cells From Multiple Donors is Heterogeneous", Journal of Cellular Biochemistry, 81(2), (2001), 312-319.
Stafford, Kristine M, et al., "Stem Cell Therapy for neurologi disorders: Tehrapeutic potential of Adipose-Derived Stem Cells", Current Drug Targets, 6, (2005), 57-62.
Stute, Norbert, et al., "Autologous serum for isolation and expansion of human mesenchymal stem cells for clinical use", Experimental Hematology 32, (2004), 1212-1225.
Yamashita, Y. M, et al., "Signaling in stem cell niches: lessons from the *Drosophila* germline", J Cell Sci., 118(Pt 4), (Feb. 15, 2005), 665-72.
Zhou, L., et al., "Analysis of the pattern of gene expression during human adipogenesis by DNA microarray", Biotechnology Techniques, 13(8), (Aug. 1999), 513-517.
Zuk, P. A, et al., "Multilineage cells from human adipose tissue: Implications for cellbased therapies", Tissue Engineering, 7(2), XP00219871 0, ISSN: 1076-3279, (Apr. 1, 2001), 211-228.
"U.S. Appl. No. 12/580,419, Final Office Action mailed May 8, 2012", 11 pgs.
"Australian Application Serial No. 2007320031, First Examiners Report mailed Apr. 10, 2012", 4 pgs.
"European Application Serial No. 07867208.6, Extended Search Report mailed Jun. 4, 2012", 7 pgs.
"Japanese Application Serial No. 2008-553314, Office Action mailed Jun. 5, 2012", With English Translation, 6 pgs.
Boquest, Andrew C, et al., "Isolation and Transcription Profiling of Purified Uncultured Human Stromal Stem Cells: Alteration of Gene Expression after In Vitro Cell Culture", Molecular Biology of the Cell vol. 16, (Mar. 2005), 11 pgs.
Johnstone, Brian, et al., "In vitro chondrogenesis of bone marrow-derived mesenchymal progenitor cells", Exp Cell Res., 238(1), (Jan. 10, 1998), 265-72.

Kelm, Jens M, et al., "Method for generation of homogeneous multicellular tumor spheroids applicable to a wide variety of cell types", Biotechnol. Bioeng., 83(2), (2003), 173-180.
Parker, A. M, et al., "Accelerated Diabetic Wound Healing in a Murine Model with the Application of Multipotent Human Adipose Derived Stem Cells", Journal of the American College of Surgeons 203(3), (Sep. 1, 2006), S43.
"U.S. Appl. No. 12/066,348, Response filed Dec. 22, 2010 to Office Action mailed Dec. 3, 2010", 6 pgs.
"U.S. Appl. No. 12/162,523, Response filed Sep. 4, 2012 to Final Office Action mailed Mar. 2, 2012", 11 pgs.
"Australian Application Serial No. 2007320031, Response filed Mar. 18, 2013 to First Examiners Report mailed Apr. 10, 2012", 10 pgs.
"European Application Serial No. 07867208.6, Response filed Dec. 21, 2012 to Extended European Search Report mailed Jun. 4, 2012", 10 pgs.
"Japanese Application Serial No. 2009-531471, Office Action mailed Sep. 4, 2012", With English Translation, 4 pgs.
"U.S. Appl. No. 12/162,523 , Response filed Jan. 19, 2012 to Non Final Office Action mailed Jul. 19, 2011", 10 pgs.
"U.S. Appl. No. 12/162,523, Final Office Action mailed Mar. 2, 2012", 12 pgs.
"U.S. Appl. No. 12/580,419, Response Filed Mar. 1, 2012 to Non Final Office Action mailed Sep. 1, 2011", 5 pgs.
"U.S. Appl. No. 12/162,523, Notice of Allowance mailed Jul. 25, 2013", 11 pgs.
"European Application Serial No. 07867208.6, Examination Notification Art. 94(3) mailed Nov. 29, 2013", 4 pgs.
Moon, Mi Hyang, et al., "Human adipose tissue-derived mesenchymal stem cells improve postnatal neovascularization in a mouse model of hindlimb ischemia", Cellular Physiology and Biochemistry, vol. 17, No. 5-6, (Jun. 20, 2006), 279-290.
Rehman, J, et al., "Secretion of angiogenic and antiapoptotic factors by human adipose stromal cells", Circulation, Lippincott Williams & Wilkins, US, vol. 109, No. 10, (Mar. 16, 2004), 1292-1298.
European Application Serial No. 07867208.6, Examination Notification Art. 94(3) mailed Apr. 7, 2014, 3 pgs.
European Application Serial No. 07867208.6, Response filed Mar. 25, 2014 to Office Action mailed Nov. 29, 2013, 9 pgs.
European Application Serial No. 07867208.6, Response filed May 2, 2014 to Office Action mailed Apr. 7, 2014, 49 pgs.

* cited by examiner

METHODS AND COMPOSITIONS USEFUL FOR DIABETIC WOUND HEALING

CROSS REFERENCE TO RELATED APPLICATIONS

This application is a national stage filing of International Application No. PCT/US2007/021432, filed Oct. 5, 2007, which claims priority under 35 U.S.C. §119(e) to U.S. Provisional Application Ser. No. 60/850,001 filed Oct. 6, 2006, the disclosures of which are incorporated by reference in their entirety herein.

STATEMENT REGARDING FEDERALLY SPONSORED RESEARCH OR DEVELOPMENT

This invention was made in part with United States Government support under Grant No. HL72141, awarded by the National institutes of Health. The United States Government has certain rights in the invention.

BACKGROUND

Mesenchymal stem cells are stem cells that can be isolated from a variety of tissues such as bone marrow, adipose tissue, dermis/skin, etc. These cells are the subject of intense scientific research and scrutiny and are thought to represent a cornerstone for potentially revolutionary paradigms of regenerative therapies of the future.

Mesenchymal stem cells in general, and adipose stem cells in particular, hold great promise for future clinical therapies which enhance the body's natural ability to heal itself. One hurdle common to the use of these potential therapies is the current practice of using fetal bovine serum or other animal sera in the culture media of cells intended for use in humans. The undefined and variable nature of animal sera, as well as the associated risk of introducing xenobiotic pathogens and triggering severe allergic responses in some subjects, presents a technical problem presently unresolved in the field.

In recent years, the identification of mesenchymal stem cells, chiefly obtained from bone marrow, has led to advances in tissue regrowth and differentiation. Such cells are pluripotent cells found in bone marrow and periosteum, and they are capable of differentiating into various mesenchymal or connective tissues. For example, such bone-marrow derived stem cells can be induced to develop into myocytes upon exposure to agents such as 5-azacytidine (Wakitani et al., Muscle Nerve, 18 (12), 1417-26 (1995)). It has been suggested that such cells are useful for repair of tissues such as cartilage, fat, and bone (see, e.g., U.S. Pat. Nos. 5,908,784, 5,906,934, 5,827,740, 5,827,735), and that they also have applications through genetic modification (see, e.g., U.S. Pat. No. 5,591,625). While the identification of such cells has led to advances in tissue regrowth and differentiation, the use of such cells is hampered by several technical hurdles. One drawback to the use of such cells is that they are very rare (representing as few as 1/2,000,000 cells), making any process for obtaining and isolating them difficult and costly. Of course, bone marrow harvest is universally painful to the donor. Moreover, such cells are difficult to culture without inducing differentiation, unless specifically screened sera lots are used, adding further cost and labor to the use of such stem cells. U.S. Pat. No. 6,200,606 (Peterson et al.) describes the isolation of CD34+ bone or cartilage precursor cells (of mesodermal origin) from tissues, including adipose.

The presence of adult multipotent "stem" cells has been demonstrated in a large number of tissues, for example the bone marrow, blood, liver, muscle, the nervous system, and in adipose tissue. Adult "stem" cells, which in theory are capable of infinite self-renewal, have great cell plasticity, i.e., the ability to differentiate into tissues other than those for which it was believed they were destined. The properties of said cells, which are similar to those of embryonic stem cells (ES), open up considerable therapeutic perspectives especially as their use does not pose the problems of compatibility and ethics, encountered with ES cells.

Adipose tissue plays an important and overlooked role in the normal development and physiology of humans and other mammalian species. Many different kinds of fat exist. The most common type is white adipose tissue, located under the skin (subcutaneous fat), within the abdominal cavity (visceral fat) and around the reproductive organs (gonadal fat). Less common in the adult human is brown adipose tissue, which plays an important role in generating heat during the neonatal period; this type of fat is located between the shoulder blades (interscapular), around the major vessels and heart (periaortic and pericardial), and above the kidney (suprarenal).

As women mature, they develop increased amounts of mammary adipose tissue. The mammary fat pad serves as an energy source during periods of lactation. Indeed, reproductive capacity and maturation are closely linked to the adipose tissue stores of the individual. Puberty in women and men correlates closely with the production and release of leptin, an adipose tissue derived hormone, and to body fat composition. Other adipose tissue sites play a structural role in the body. For example, the mechanical fat pads in the soles of the feet provide a cushion against the impact of walking. Loss of this fat depot leads to progressive musculoskeletal damage and impaired mobility. Bone marrow fat cells are present in bone marrow to provide energy to developing blood cells within the marrow.

Bone marrow adipocytes are different from adipocytes present in adipose tissue, differing in morphology, physiology, biochemistry as well as their response to various stimulators such as insulin. Adipocytes present in bone marrow stroma may function to: 1) regulate the volume of hemodynamically active marrow; 2) serve as a reservoir for lipids needed in marrow cell proliferation, and 3) may be developmentally related to other cell lineages such as osteoblasts. White adipose tissue (i.e. body fat) in contrast, is involved in lipid metabolism and energy homeostasis (Gimble, "The Function of Adipocytes in the Bone Marrow Stroma", The New Biologist 2(4), 1990, pp. 304-312).

The vast majority of research related to various stem cell populations has centered on their behavior and therapeutic potential as adherent cell cultures and/or single cell suspensions that are either mixed in nature, or clonally derived. However, a consensus is evolving, supported by promising evidence, that stem cells most likely exist in vivo within the context of a supportive niche, or microenvironment.

As reviewed in several recent papers, emerging data suggest that "it is the combination of the intrinsic characteristics of stem cells and their microenvironment that shapes their properties and defines their potential" (Fuchs et al., Cell, 116:769-778, 2004). In essence, the specific cellular environment, or niche, is composed of a diverse, heterogeneous collection of cells (in addition to, or including the stem cell constituents) that create/provide a milieu of soluble and matrix factors. These factors help to direct and control the homeostasis of the stem cell reservoir, including cell growth, differentiation, and renewal (Kindler, J. Leukocyte Biol., 78:836-844, 2005; Fuchs et al., Cell, 116:769-778, 2004). And while it is currently thought that the majority of stem cells are dormant/quiescent in the $G_0$ phase of the cell cycle when a tissue/niche is in equilibrium, it is also believed that loss of, or damage to a tissue/niche provides a powerful stimulus to the stem cell reservoir to re-establish equilibrium (i.e., repair; regenerate) by renewal (expansion) and/or differentiation. This capacity likely involves asymmetric cell division and possibly some degree of dedifferentiation, all of which is thought to be governed by the niche micromilieu.

Given the above background, it becomes clear that the 'creation' of ex vivo stem cell niche models would be highly useful and valuable for the study of stem cell biology, as well as for potential therapeutic applications. Researchers have described and characterized in vitro 'niches' for embryonic stem cells (embryoid bodies) and neural stem cells (neurospheres)—which both involve suspension (i.e., non-adherent) culture of said cells in multicellular aggregates. However, no such 'system' has been described for mesenchymal stem/stromal cells, particularly adipose-derived cells. This is likely due to the difficulty in culturing these cells in suspension, as they are extremely adherent, even to surfaces that are supposedly unfavorable to cell culture/adherence.

There is a long felt need in the art for methods to enhance wound healing and tissue repair, particularly in diabetic subjects. The present invention satisfies this need.

BRIEF SUMMARY OF THE INVENTION

The present invention provides methods and compositions to grow and differentiate adipose tissue-derived stem cell subpopulations and to use them to enhance wound repair in a subject in need thereof. In one aspect, the cells are human cells. In one aspect, the subject is a human. In one aspect, the wound is in a diabetic subject.

In one embodiment, the invention encompasses administering an effective amount of ASC cells directly to a wound in a subject in need thereof. In one aspect, the wound is associated with diabetes. In one aspect, the wound associated with diabetes is a skin lesion. In one aspect, the wound is covered with a dressing following administration of ASC cells. In another aspect, the invention encompasses applying ASC cells directly to a dressing and then applying the dressing. In one aspect, the dressing is one such as the Tegaderm™ impermeable dressing. Tegaderm™ is a transparent medical dressing manufactured by 3M. Tegaderm transparent dressings can be used to cover and protect, for example, catheter sites and wounds. In one aspect, the dressing is a sterile, waterproof bacterial barrier which consists of a non-adherent absorbent pad bonded to a larger thin film transparent dressing. In one aspect, when the dressing is applied first, the cells are injected beneath the dressing. In one aspect, the cells are injected through the dressing.

In one aspect, the wound is chronic. In another aspect, it is acute.

In one embodiment, the ASC cells are administered in a single cell suspension. In another aspect, the cells are administered as aggregates of cells. In one aspect, the aggregates are SOM-Bs. In one aspect, the cells have been induced to differentiate prior to being administered to the subject. In one aspect, the cells have been purified before being administered to the subject. In one aspect, the ASCs have been immortalized. In one aspect, two or more groups of ASCs are administered. In one aspect, the two or more groups of ASCs are not the same. In one aspect, one of the two or more groups is obtained from a different culture or has been induced to differentiate. In one aspect, at least one cell type other than an ASC is administered in combination with the ASC. In one aspect, the other cell type is a keratinocyte or a dermal fibroblast.

In one embodiment, at least one other cell type other than an ASC is included in the SOM-B or is administered with the SOM-B. In one aspect, the other cell type is a keratinocyte or a dermal fibroblast. For example, while the SOM-Bs are being formed in culture, another cell type such as a keratinocyte or dermal fibroblast is added to the culture so that the at least one other cell type is incorporated into the SOM-B.

In one embodiment, at least one million cells are administered. In another embodiment, at least 100 million cells are administered. In one aspect, at least one million cells are delivered at least twice. In one aspect, they are delivered twice per day. In another aspect, at least 100 million cells are delivered at least twice per day.

In one embodiment, cells of the invention can be used in conjunction with, or administered with, a product such as Alloderm or other acellular scaffolds.

In one embodiment, cells of the invention can be used in conjunction with a product such as Dermagraft.® Dermagraft® is indicated for use in the treatment of full-thickness diabetic foot ulcers greater than six weeks duration, which extend through the dermis, but without tendon, muscle, joint capsule, or bone exposure. Dermagraft® is a cryopreserved human fibroblast-derived dermal substitute; it is composed of fibroblasts, extracellular matrix, and a bioabsorbable scaffold. Dermagraft® is manufactured from human fibroblast cells derived from newborn foreskin tissue. During the manufacturing process, the human fibroblasts are seeded onto a bioabsorbable polyglactin mesh scaffold. The fibroblasts proliferate to fill the interstices of this scaffold and secrete human dermal collagen, matrix proteins, growth factors, and cytokines to create a three-dimensional human dermal substitute containing metabolically active living cells. Dermagraft® does not contain macrophages, lymphocytes, blood vessels, or hair follicles.

In one embodiment, conditioned medium obtained from culturing ASCs in growth medium is used to treat wounds. In one aspect, the ASCs are aggregates of cells. In one aspect, the aggregates are SOM-Bs. In one aspect, the medium is serum-free. In one aspect, the medium added to the cells contains no proteins other than human proteins. In one aspect, conditioned medium is obtained and then concentrated. In one aspect, the conditioned medium is purified to remove contaminants or to increase the concentration of a factor(s) of interest. In one aspect, the conditioned medium contains at least two growth factors. One of ordinary skill in the art will appreciate that there are many techniques available for concentrating or purifying the proteins and growth factors that are secreted into growth medium by cells. In one aspect, the ASCs are SOM-Bs (i.e., SNiMs). In one aspect, the cells are induced to differentiate prior to conditioned medium being prepared. In one aspect, the conditioned medium is administered in combination with ASCs.

It will be appreciated that cells of the invention can be administered using various kinds of delivery systems and media. Furthermore, cells of the invention can be administered in combination with other therapeutic agents and compounds and can be used with other kinds of treatments.

In one embodiment, an effective amount of at least one growth factor, cytokine, hormone, or extracellular matrix compound or protein useful for enhancing wound healing is administered with the cells of the invention. In one aspect, a combination of these agents is used. In one aspect, growth factors useful in the practice of the invention include, but are not limited to, GCSF, IL6, IL8, IL10, MCP1, MCP2, Tissue Factor, FGFb, KGF, VEGF, PLGF, MMP1, MMP9, TIMP1, TIMP2, TGFβ1, and HGF. In one aspect, the growth factors, cytokines, hormones, and extracellular matrix compounds and proteins are human.

In one aspect, the extracellular matrix protein is collagen. The extracellular matrix component can be derived from an exogenous source, or can be generated by the cell of the invention.

In one embodiment, SOM-B-generated extracellular matrix is administered to a wound after removal and/or devitalization of the cellular constituents.

Various aspects and embodiments of the invention are described in further detail below.

DETAILED DESCRIPTION OF THE INVENTION

Abbreviations and Acronyms

Figure 1:
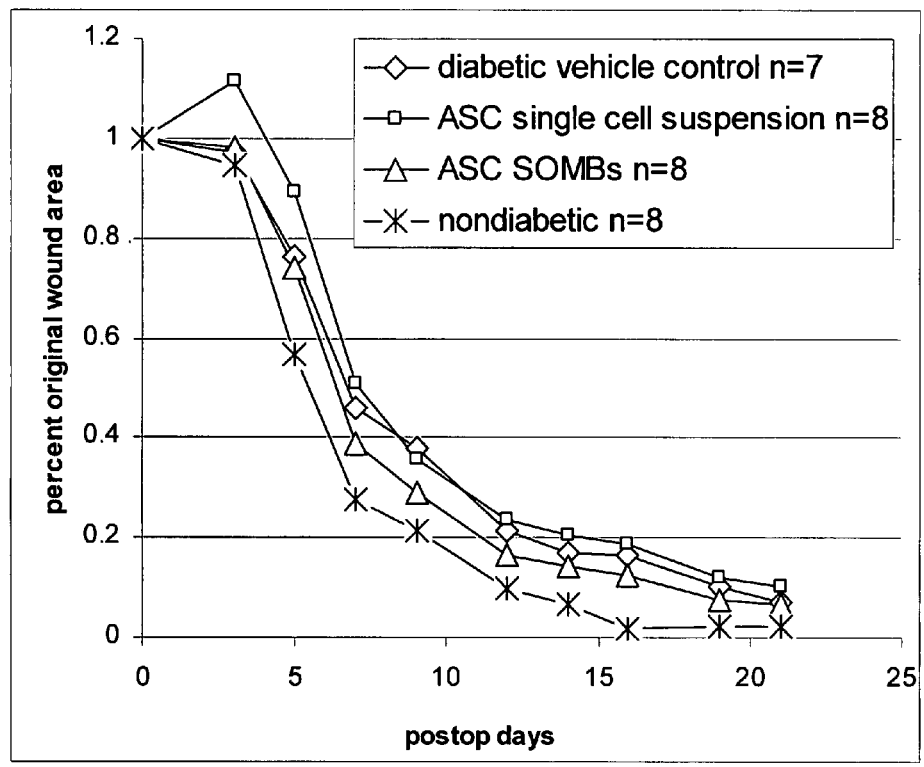
FIG. 1 graphically illustrates the results of a diabetic wound healing trial using ASCs. The group marked with ♦ represents the diabetic vehicle control group (n=7). The group marked with ■ represents ASC in single cell suspension (n=8). The group marked with x represents the nondiabetic group. The group marked with ▲ the group receiving ASCs in the form of SOMBs. The ordinate represents the percentage of the original wound area and the abscissa represents post-operative time in days.
Figure 2:
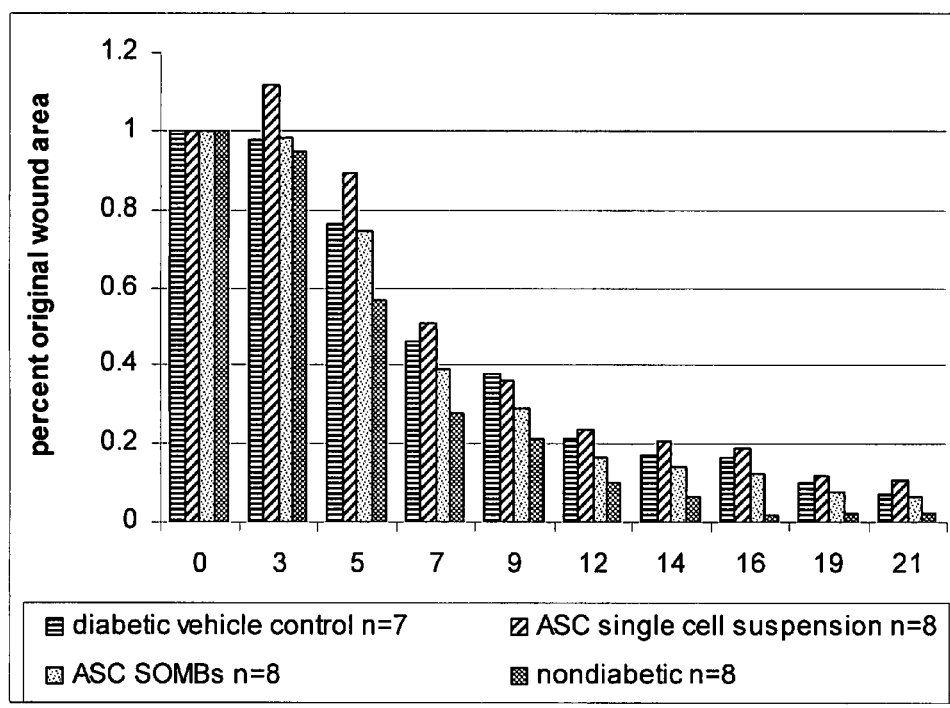
FIG. 2 represents a bar graph illustrating the results of a diabetic wound healing trial using ASCs. There were four groups. The left (first) bar of each time point represents the diabetic vehicle control (n=7; horizontal hatching on bars). The second bar represents treatment with ASC cells in single suspension (n=8; single diagonal hatching on bars). The third bar represents treatment with ASC in the form of SOMBs (n=8; stippled bars). The fourth bar represents the nondiabetic group (n=8; double diagonal hatching on bars).
Figure 3A:
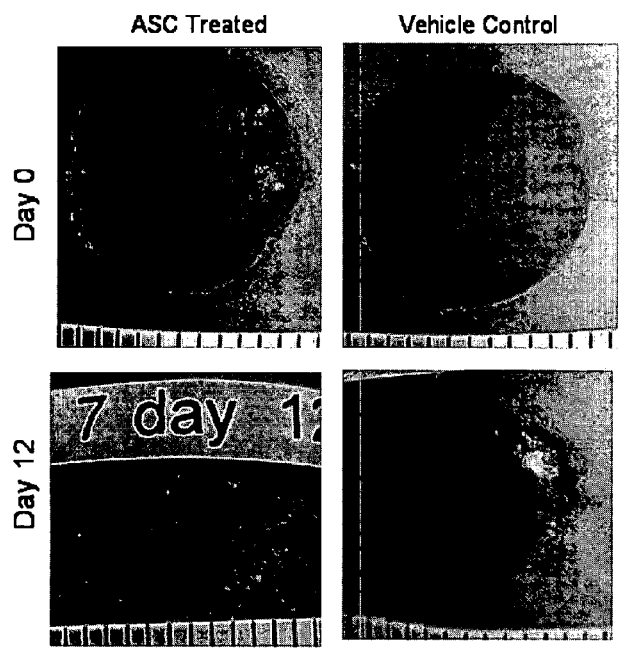
FIG. 3, comprising a left panel (FIG. 3A) and a right panel (FIG. 3B), illustrates the efficacy of using human ASCs in an animal model of delayed healing (db/db mice). The left panel of Figure comprises images of four photographs showing ASC treated (left two images) or vehicle control treated (right two images) on day 0 of treatment (upper two images) and on day 12 of treatment (lower two images). The right panel is a graphic illustration of the effect of ASC aggregate or ASC suspension treatment of db/db mice. The four groups are: db/-control, db/db untreated, hASC cell aggregate, and hASC cell suspension.
Figure 3B:
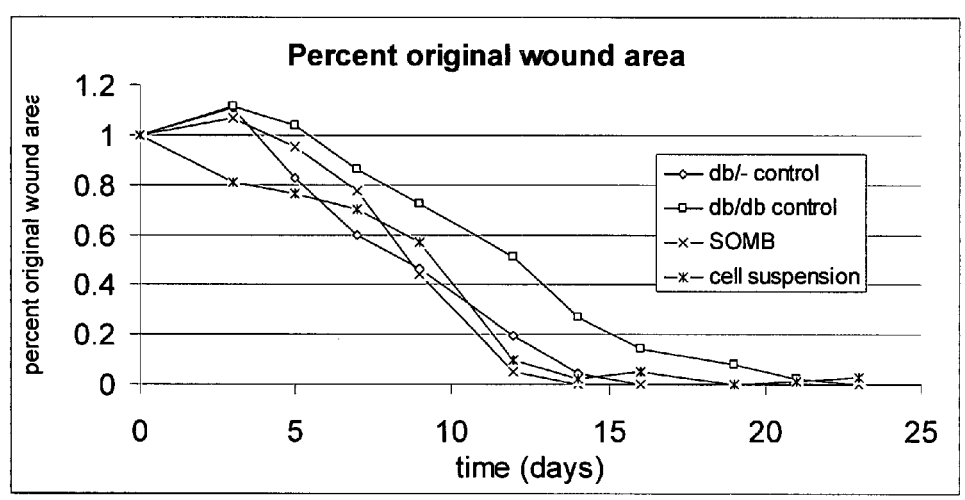
Figure 4:
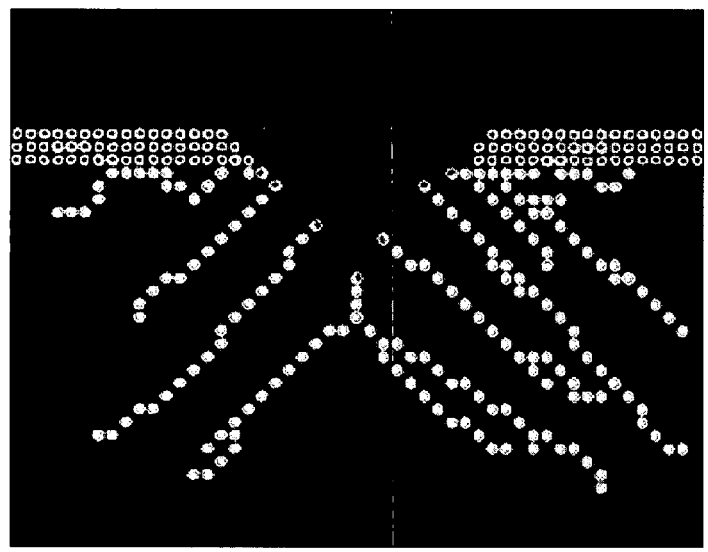
FIG. 4 is a schematic representation of a 2-D agent-based model of a wound bed for use in studying the effects of various cell delivery schemes.
Figure 5:
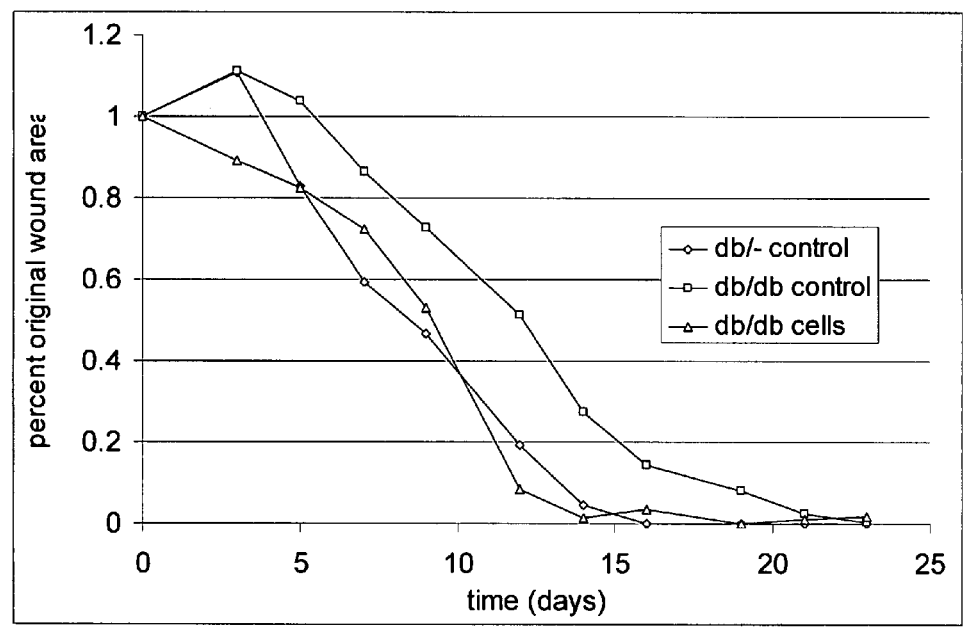
FIG. 5 graphically illustrates the results of an experiment comparing a diabetic group treated with cells and a vehicle control. The three groups in the figure are: ♦ represents the db/-control; ■ represents the db/db control; and ▲ represents a diabetic group treated with cells of the invention. The ordinate represents percent of the original wound area and the abscissa represent time (in days) from the start of treatment.
Figure 6:
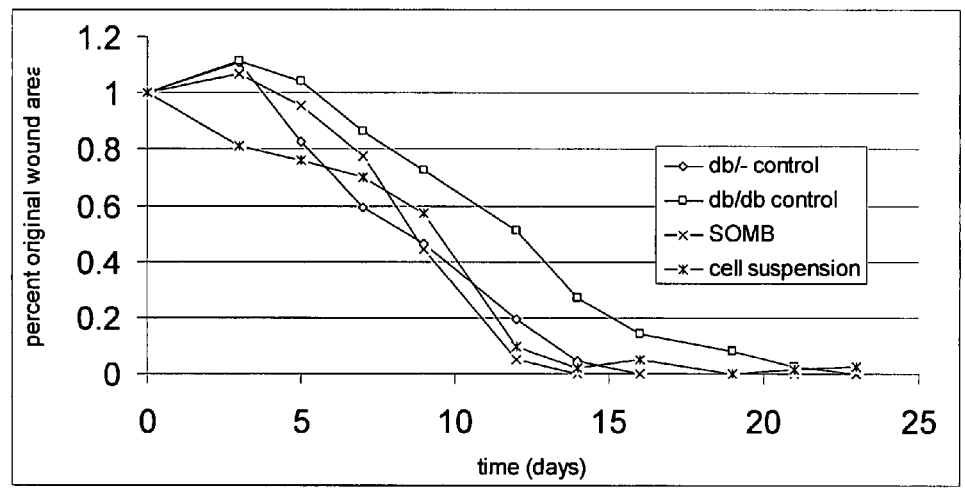
FIG. 6 graphically illustrates the results of an experiment comparing a diabetic group treated with a cell suspension or SOMBs. ♦ represents the db/-control. ■ represents the db/db control. x represents the SOMB-treated group. ● represents the group treated with a cell suspension. The ordinate represents percent of the original wound area and the abscissa represent time (in days) from the start of treatment. When comparing diabetic cell treated and vehicle to control-day 12 p<0.001; and on days 14 and 19, p<0.05.
Figure 7:
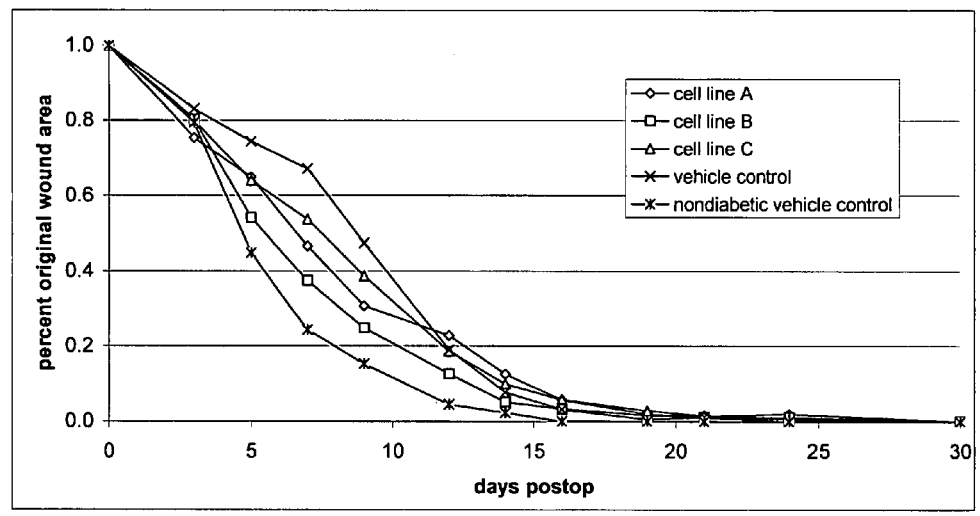
FIG. 7 graphically illustrates the results of an experiment demonstrating the effects of adipose stem cells on diabetic wound healing. Five groups were treated as follows: cell line A; cell line B; cell line C; vehicle control; nondiabetic vehicle control. The ordinate represents the percentage of the original wound area and the abscissa represents days post-procedure.

ASC—adipose tissue-derived stem cell
ASCB—adipose stem/stromal cell blastema
ASC-MB—ASC-mesenchymal blastema or mesenchoid body
CB—chimeric blastema
DMEM—Dulbecco's modified Eagle's medium ECM—extracellular matrix
ES—embryonic stem cell
FACS—fluorescent activated cell sorting
FBS—fetal bovine serum
FGF—fibroblast growth factor
gf—growth factor
HSC—hematopoietic stem cell
HS—human serum (also referred to as HmS herein)
HSA—human serum albumin
IL-1β-interleukin-1 beta
MB—mesenchoid body
PDGF—platelet-derived growth factor
PLA—processed lipoaspirate cells
SCGF-β—stem cell growth factor-β
SFM—serum-free medium (also referred to as sf herein)
SNiM—Self-organizing Niche Milieu, which is another term for ASC aggregates
SOM-B—Self-Organizing Mesenchymal Blastema (also referred to as "self-organizing mesenchoid bodies" and as SNiM herein)
TNFα—tumor necrosis factor alpha
ULA—ultra low attachment tissue culture plate
VEGF—Vascular endothelial growth factor

| Abbreviations and Acronyms | |
|---|---|
| ASC- | adipose tissue-derived stem cell |
| ASCB- | adipose stem/stromal cell blastema |
| ASC-MB- | ASC-mesenchymal blastema or mesenchoid body |
| CB- | chimeric blastema |
| DMEM- | Dulbecco's modified Eagle's medium |
| ECM- | extracellular matrix |
| ES- | embryonic stem cell |
| FACS- | fluorescent activated cell sorting |
| FBS- | fetal bovine serum |
| FGF- | fibroblast growth factor |
| gf- | growth factor |
| HSC- | hematopoietic stem cell |
| HS- | human serum (also referred to as HmS herein) |
| HSA- | human serum albumin |
| IL-1β- | interleukin-1 beta |
| MB- | mesenchoid body |
| PDGF- | platelet-derived growth factor |
| PLA- | processed lipoaspirate cells |
| SCGF-β- | stem cell growth factor-β |
| SFM- | serum-free medium (also referred to as sf herein) |
| SNiM- | Self-organizing Niche Milieu, which is another term for ASC aggregates |
| SOM-B- | Self-Organizing Mesenchymal Blastema (also referred to as "self-organizing mesenchoid bodies" and as SNiM herein) |
| TNFα- | tumor necrosis factor alpha |
| ULA- | ultra low attachment tissue culture plate |
| VEGF- | Vascular endothelial growth factor |

DEFINITIONS

In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

Adipose-derived stem cells (ASC) or "adipose-derived stromal cells" refer to cells that originate from adipose tissue. By "adipose" is meant any fat tissue. The adipose tissue may be brown or white adipose tissue, derived from subcutaneous, omental/visceral, mammary, gonadal, or other adipose tissue site. Preferably, the adipose is subcutaneous white adipose tissue. Such cells may comprise a primary cell culture or an immortalized cell line. The adipose tissue may be from any organism having fat tissue. Preferably, the adipose tissue is mammalian, more preferably, the adipose tissue is human. A convenient source of adipose tissue is from liposuction surgery, however, the source of adipose tissue or the method of isolation of adipose tissue is not critical to the invention. The term ASC-SOM-B (SNiM) is meant to reinforce the fact that SOM-Bs (SNiMs) as described herein are derived from ASCs.

The term "adult" as used herein, is meant to refer to any non-embryonic or non-juvenile subject. For example the term "adult adipose tissue stem cell," refers to an adipose stem cell, other than that obtained from an embryo or juvenile subject.

A disease or disorder is "alleviated" if the severity of a symptom of the disease, condition, or disorder, or the frequency with which such a symptom is experienced by a subject, or both, are reduced.

As used herein, an "analog" of a chemical compound is a compound that, by way of example, resembles another in structure but is not necessarily an isomer (e.g., 5-fluorouracil is an analog of thymine).

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

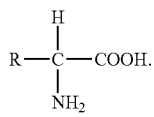

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid as used herein, refers to amino acids in which the R groups have a net positive charge at pH 7.0, and include, but are not limited to, the standard amino acids lysine, arginine, and histidine.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies.

As used herein, the term "antisense oligonucleotide" or antisense nucleic acid polymer means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the invention include, but are not limited to, phosphorothioate oligonucleotides and other modifications of oligonucleotides.

The term "autologous", as used herein, refers to something that occurs naturally and normally in a certain type of tissue or in a specific structure of the body.

In transplantation, it refers to a graft in which the donor and recipient areas are in the same individual, or to blood that the donor has previously donated and then receives back, usually during surgery.

The term "basal medium", as used herein, refers to a minimum essential type of medium, such as Dulbecco's Modified Eagle's Medium, Ham's F12, Eagle's Medium, RPMI, AR8, etc., to which other ingredients may be added. The term does not exclude media which have been prepared or are intended for specific uses, but which upon modification can be used for other cell types, etc.

The term "biocompatible," as used herein, refers to a material that does not elicit a substantial detrimental response in the host.

The term "biodegradable," as used herein, means capable of being biologically decomposed. A biodegradable material differs from a non-biodegradable material in that a biodegradable material can be biologically decomposed into units which may be either removed from the biological system and/or chemically incorporated into the biological system.

The term "bioresorbable," as used herein, refers to the ability of a material to be resorbed in vivo. "Full" resorption means that no significant extracellular fragments remain. The resorption process involves elimination of the original implant materials through the action of body fluids, enzymes, or cells. Resorbed calcium carbonate may, for example, be redeposited as bone mineral, or by being otherwise re-utilized within the body, or excreted. "Strongly bioresorbable," as the term is used herein, means that at least 80% of the total mass of material implanted is resorbed within one year.

The term "blastema," as used herein, encompasses inter alia, the primordial cellular mass from which an organ, tissue, or part is formed as well as a cluster of cells competent to initiate and/or facilitate the regeneration of a damaged or ablated structure.

The phrases "cell culture medium," "culture medium" (plural "media" in each case) and "medium formulation" refer to a nutritive solution for cultivating cells and may be used interchangeably.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

A "pathoindicative" cell, tissue, or sample is one which, when present, is an indication that the animal in which the cell, tissue, or sample is located (or from which the tissue was obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

A "compound," as used herein, refers to any type of substance or agent that is commonly considered a drug, or a candidate for use as a drug, combinations, and mixtures of the above, as well as polypeptides and antibodies of the invention.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

The term "delivery vehicle" refers to any kind of device or material which can be used to deliver cells in vivo or can be added to a composition comprising cells administered to an animal. This includes, but is not limited to, implantable devices, aggregates of cells, matrix materials, gels, etc.

As used herein, a "derivative" of a compound refers to a chemical compound that may be produced from another compound of similar structure in one or more steps, as in replacement of H by an alkyl, acyl, or amino group.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, an "effective amount" means an amount sufficient to produce a selected effect.

The term "feeder cells" as used herein refers to cells of one type that are co-cultured with cells of a second type, to provide an environment in which the cells of the second type can be maintained, and perhaps proliferate. The feeder cells can be from a different species than the cells they are supporting. Feeder cells can be non-lethally irradiated or treated to prevent their proliferation prior to being co-cultured to ensure to that they do not proliferate and mingle with the cells which they are feeding. The terms, "feeder cells", "feeders," and "feeder layers" are used interchangeably herein.

As used herein, a "functional" molecule is a molecule in a form in which it exhibits a property or activity by which it is characterized.

A "fragment" or "segment" is a portion of an amino acid sequence, comprising at least one amino acid, or a portion of a nucleic acid sequence comprising at least one nucleotide. The terms "fragment" and "segment" are used interchangeably herein.

"Graft" refers to any free (unattached) cell, tissue, or organ for transplantation.

"Allograft" or "allogeneic" refers to a transplanted cell, tissue, or organ derived from a different animal of the same species.

"Xenograft" or "xenogeneic" refers to a transplanted cell, tissue, or organ derived from an animal of a different species.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the) (BLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

Used interchangeably herein are the terms "isolate" and "select".

The term "isolated," when used in reference to cells, refers to a single cell of interest, or population of cells of interest, at least partially isolated from other cell types or other cellular material with which it naturally occurs in the tissue of origin (e.g., adipose tissue). A sample of stem cells is "substantially pure" when it is at least 60%, or at least 75%, or at least 90%, and, in certain cases, at least 99% free of cells other than cells of interest. Purity can be measured by any appropriate method, for example, by fluorescence-activated cell sorting (FACS), or other assays which distinguish cell types.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

As used herein, a "ligand" is a compound that specifically binds to a target compound. A ligand (e.g., an antibody) "specifically binds to" or "is specifically immunoreactive with" a compound when the ligand functions in a binding reaction which is determinative of the presence of the compound in a sample of heterogeneous compounds. Thus, under designated assay (e.g., immunoassay) conditions, the ligand binds preferentially to a particular compound and does not bind to a significant extent to other compounds present in the sample. For example, an antibody specifically binds under immunoassay conditions to an antigen bearing an epitope against which the antibody was raised. A variety of immunoassay formats may be used to select antibodies specifically immunoreactive with a particular antigen. For example, solid-phase ELISA immunoassays are routinely used to select monoclonal antibodies specifically immunoreactive with an antigen. See Harlow and Lane, 1988, *Antibodies, A Laboratory Manual*, Cold Spring Harbor Publications, New York, for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

The term "modulate", as used herein, refers to changing the level of an activity, function, or process. The term "modulate" encompasses both inhibiting and stimulating an activity, function, or process.

The term "progeny" of a stem cell as used herein refers to a cell which is derived from a stem cell and may still have all of the differentiation abilities of the parental stem cell, i.e., multipotency, or one that may no longer be multipotent, but is now committed to being able to differentiate into only one cell type, i.e., a committed cell type. The term may also refer to a differentiated cell.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. A "significant detectable level" is an amount of contaminate that would be visible in the presented data and would need to be addressed/explained during analysis of the forensic evidence.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "secondary antibody" refers to an antibody that binds to the constant region of another antibody (the primary antibody).

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

The term "inhibit," as used herein, refers to the ability of a compound of the invention to reduce or impede a described function. Preferably, inhibition is by at least 10%, more preferably by at least 25%, even more preferably by at least 50%, and most preferably, the function is inhibited by at least 75%.

The term "ingredient" refers to any compound, whether of chemical or biological origin, that can be used in cell culture media to maintain or promote the proliferation, survival, or differentiation of cells. The terms "component," "nutrient", "supplement", and ingredient" can be used interchangeably and are all meant to refer to such compounds. Typical non-limiting ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

The term "inhibit," as used herein, means to suppress or block an activity or function such that it is lower relative to a control value. The inhibition can be via direct or indirect mechanisms. In one aspect, the activity is suppressed or blocked by at least 10% compared to a control value, more preferably by at least 25%, and even more preferably by at least 50%.

The term "inhibitor" as used herein, refers to any compound or agent, the application of which results in the inhibition of a process or function of interest, including, but not limited to, differentiation and activity. Inhibition can be inferred if there is a reduction in the activity or function of interest.

The term "injury" refers to any physical damage to the body caused by violence, accident, trauma, or fracture, etc.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

A "reversibly implantable" device is one which may be inserted (e.g. surgically or by insertion into a natural orifice of the animal) into the body of an animal and thereafter removed without great harm to the health of the animal.

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

The term "standard," as used herein, refers to something used for comparison. For example, a standard can be a known standard agent or compound which is administered or added to a control sample and used for comparing results when measuring said compound in a test sample. Standard can also refer to an "internal standard," such as an agent or compound which is added at known amounts to a sample and is useful in determining such things as purification or recovery rates when a sample is processed or subjected to purification or extraction procedures before a marker of interest is measured.

The term "stimulate" as used herein, means to induce or increase an activity or function level such that it is higher relative to a control value. The stimulation can be via direct or indirect mechanisms. In one aspect, the activity or differentiation is stimulated by at least 10% compared to a control value, more preferably by at least 25%, and even more preferably by at least 50%. The term "stimulator" as used herein, refers to any compound or agent, the application of which results in the stimulation of a process or function of interest, including, but not limited to, ASC cell production, differentiation, and activity, as well as that of ASC progeny.

A "subject" of analysis, diagnosis, or treatment is an animal. Such animals include mammals, preferably a human.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

As used herein, the term "treating" includes prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "treating" includes prophylaxis of the specific disease, disorder, or condition, or alleviation of the symptoms associated with a specific disease, disorder, or condition and/or preventing or eliminating said symptoms.

As used herein, the term "wound" relates to a physical tear, break, or rupture to a tissue or cell layer. A wound may occur by any physical insult, including a surgical procedure or as a result of a disease, disorder condition.

EMBODIMENTS

The present application is based on the finding disclosed herein that adipose tissue-derived cells are useful in treating wounds, i.e., enhancing the healing of wounds.

The cells of the invention provide advantages such as translatability, reproducibility, and predictability in their use. Additional advantageous characteristics of the cells and methods of the invention include:

ability to culture/manufacture in defined, serum-free conditions, with no foreign proteins (i.e., no FBS);

enhanced production of growth factors compared to monolayer cultured cells;

self-generated matrix, no need for bovine collagen or other xenogeneic ECM components;

immediately implantable, with no need to trypsinize;

extensive replicative capacity;

less variability, more predictable biology than cells grown as monolayer cultures;

robust (hypoxia; anoikis), able to survive implantation in vivo better;

dynamic (respond to environment); and amenable to automated scale-up.

Adult human extramedullary adipose tissue-derived stromal cells represent a stromal stem cell source that can be harvested routinely with minimal risk or discomfort to the patient. Pathologic evidence suggests that adipose-derived stromal cells are capable of differentiation along multiple lineage pathways. Adipose tissue is readily accessible and abundant in many individuals. Obesity is a condition of epidemic proportions in the United States, where over 50% of adults exceed the recommended BMI based on their height.

It is well documented that adipocytes are a replenishable cell population. Even after surgical removal by liposuction or other procedures, it is common to see a recurrence of adipocytes in an individual over time. This suggests that adipose tissue contains stromal stem cells that are capable of self-renewal.

Adipose tissue offers many practical advantages for tissue engineering applications. First, it is abundant. Second, it is accessible to harvest methods with minimal risk to the patient. Third, it is replenishable. While stromal cells represent less than 0.01% of the bone marrow's nucleated cell population, there are up to $8.6 \times 10^4$ stromal cells per gram of adipose tissue (Sen et al., 2001, Journal of Cellular Biochemistry 81:312-319). Ex vivo expansion over 2 to 4 weeks yields up to 500 million stromal cells from 0.5 kilograms of adipose tissue. These cells can be used immediately or cryopreserved for future autologous or allogeneic applications.

Adipose derived stromal cells also express a number of adhesion and surface proteins. These include, but are not limited to, cell surface markers such as CD9; CD29 (integrin beta 1); CD44 (hyaluronate receptor); CD49d,e (integrin alpha 4, 5); CD54 (ICAM1); CD55 (decay accelerating factor); CD105 (endoglin); CD106 (VCAM-1); CD166 (AL-CAM) and HLA-ABC (Class I histocompatibility antigen); and cytokines such as interleukins 6, 7, 8, 11; macrophage-colony stimulating factor; GM-colony stimulating factor; granulocyte-colony stimulating factor; leukemia inhibitory factor; stem cell factor and bone morphogenetic protein. Many of these proteins have the potential to serve a hematopoietic supportive function and all of them are shared in common by bone marrow stromal cells.

The adipose tissue-derived stromal cells useful in the methods of invention can be isolated by a variety of methods known to those skilled in the art such as described in WO 00/53795. In a preferred method, adipose tissue is isolated from a mammalian subject, preferably a human subject. A preferred source of adipose tissue is omental adipose. In humans, the adipose is typically isolated by liposuction. If the cells of the invention are to be transplanted into a human subject, it is preferable that the adipose tissue be isolated from that same subject to provide for an autologous transplant. Alternatively, the transplanted cells are allogeneic.

Many techniques are known to those of ordinary skill in the art which can be used to help isolate, culture, induce differentiation, and to characterize the cells of the invention (Gorio et al., 2004, Neuroscience, 125:179-189; Yamashita et al., 2005, J. Cell Sci., 118:665-672; Conley et al., 2004, The International Journal of Biochemistry and Cell Biology, 36:555-567; Kindler, 2005, Journal of Leukocyte Biology, 78:836-844; Fuchs et al., 2004, Cell, 116:769-778; Campos, 2004, Journal of Neuroscience Research, 78:761-769; Dontu et al., 2005, Journal of Mammary Gland Biology and Neoplasia, 10:75-86).

While it is important to treat any condition in which the potential for cell or tissue damage exists immediately (e.g., an acute wound), it is essential that certain conditions be treated before they become chronic conditions. Chronic diseases are a challenge to the patient, the health care professional, and to the health care system. They significantly impair the quality of life for millions of people in the United States. Intensive treatment is required with a high cost to society in terms of lost productivity and health care dollars. The management of chronic diseases can place an enormous strain on health care resources. Diseases or conditions, for example, wounds that were once acute but have progressed to chronic often do so because the diseases cannot be controlled or treated with known therapies. Therefore, there is a need for improved therapies for treating chronic diseases and conditions characterized by cell and tissue damage.

In one aspect, the invention provides methods for determining the optimal number of cells required for forming various sized SOM-Bs. In one aspect, the SOM-B is considered an "effective" SOM-B, where effective means capable of displaying the desired characteristics of growth, polarization, differentiation capacity, etc. The invention also provides methods for determining where cell growth is occurring in the SOM-B, what kind of matrix is being produced, where the matrix is being produced, and how much matrix is being produced. Methods are known in the art for determining the above-described properties, as well as for measuring such characteristics as cell growth rate, etc.

Methods are also known in the art which can be used to determine how frequently SOM-Bs can spawn adherent cells and the characteristics of those spawned cells, such as growth rate, ability to reach confluency, developmental plasticity, etc. Methods are also available which can be used to determine frequency of SOM-B fusion and for measuring the resulting size, shape, polarity, etc. Methods are also known in the art to test whether the SOM-Bs are multipotential or plastic, that is, do they have the ability to differentiate into more than one cell type. Such studies can be performed using suspension, adherent, or spawned cells. Cellular phenotypes which can be studied include, but are not limited to, adipocytes, bone, cartilage, skeletal muscle, cardiac muscle, neural cells such as neurons, pancreatic islet cells, and endothelial cells.

Methods and reagents are also available for characterizing SOMBs, such as methods and reagents for performing immunocharacterization, including, but not limited to the markers and proteins: Oct 4, SSEA 3, SSEA 4, CD34, CD133, CD184, NG2, ABCG2, Nestin, MyoD, NKx2.5, Laminin, Beta1 integrin, Cbfa1, Collagen type II, MAP K, HLA-1 control, Insulin, Gata, Pax, Wnt, and other transcription factors and proteins. Flow cytometry markers include, CD34, NG2, ABCG2, CXCR4, CD271, CD140b, CD105, ALDH and HLA-1.

The present invention also provides methods for using SOMBs in vivo, and various techniques for using SOMBs in vivo are known to those of ordinary skill in the art. For example, SOMBs can be administered to a subject by various routes, including topically, subcutaneously, intramuscular, and direct administration. The SOMBs of the invention have a variety of uses, including, but not limited to, vascular remodeling, bone growth and regeneration, replacement use for tissues/cells such as pancreas/islets, central nervous system, skin repair and wound healing, peripheral nervous system, wounds, tendons, ligaments, muscle, organs such as liver and kidney, and lymph nodes, as well as in engraftment procedures.

The SOM-Bs and the compositions and methods described herein also have use for regenerative therapies utilizing SOM-B-derived extracellular matrix, which has been processed and/or purified, with or without cells.

Several real or potential advantages may be offered by administering ASCs prefabricated as 3-D niches (blastemas) as compared to more traditional single cell suspensions, including:
  the cells have well-established cell-cell contacts and cell-matrix contacts, and are therefore less prone to anoikis. Anoikis is defined as programmed cell death induced by the loss of cell-matrix interactions, or by inappropriate cell-matrix interactions. (Valentijn et al., 2004; Michel, 2003). Anoikis may play a critical role in the low delivery and engraftment efficiency associated with various methods of cell delivery. Cell-to-cell interactions have been shown to be important for the differentiation of stem cells into various lineages, such as cardiomyocytes for example (Li et al., 2006);
  the cells have generated their own extracellular matrix milieu and (presumably) associated growth factors (Wang et al., 2004);
  "strength in numbers": the cells are able to survive and withstand severe in vitro conditions (such as serum-free culture) that are lethal to single cells in monolayer culture;
  the cells are able to survive as a 3-D structure by diffusion (in culture) and presumably would be able to do the same after implantation to a wound/traumatic environment; and
  the cells retain the capacity to proliferate, migrate and/or morph in response to various external stimuli, suggesting they have the potential for dynamic interaction within an injured tissue milieu.

As used herein, the term "wound" relates to a physical tear or rupture to a tissue or cell layer, including ulcers. A wound may occur by any physical insult, including a surgical procedure.

Methods for measuring wound healing are known in the art. Methods for measuring cell survival are known in the art and include various cellular, molecular, biochemical, and histological techniques.

In accordance with one embodiment of the invention, compositions comprising cells and compounds of the invention are used to enhance wound healing, and/or treat patients having deficient wound healing.

Existing wound healing formulations can also be used as pharmaceutically acceptable carriers for the procedures described herein.

The cells of the present invention may be administered to a subject alone or in admixture with a composition useful in the repair of wounds and other defects. Such compositions include, but are not limited to bone morphogenetic proteins, hydroxyapatite/tricalcium phosphate particles (HA/TCP), gelatin, poly-L-lysine, and collagen.

In one embodiment, the invention provides a method of promoting the closure of a wound within a subject using cells and compositions as described herein. In accordance with the method, the inventive cells which have been selected or have been modified to secrete a hormone, growth factor, or other agent are transferred to the vicinity of a wound under conditions sufficient for the cell to produce the hormone, growth factor or other agent. The presence of the hormone, growth factor, or other agent in the vicinity of the wound promotes closure of the wound. In one aspect, proliferation of the administered cells promotes healing of the wound. In one aspect, differentiation of the administered cells promotes healing of the wound. The method promotes closure of both external (e.g., surface) and internal wounds. Wounds to which the present inventive method is useful in promoting closure include, but are not limited to, abrasions, avulsions, blowing wounds, burn wounds, contusions, gunshot wounds, incised wounds, open wounds, penetrating wounds, perforating wounds, puncture wounds, seton wounds, stab wounds, surgical wounds, subcutaneous wounds, diabetic lesions, or tangential wounds. The method need not achieve complete healing or closure of the wound; it is sufficient for the method to promote any degree of wound closure. In this respect, the method can be employed alone or as an adjunct to other methods for healing wounded tissue.

The present invention encompasses a method of treating a disorder amenable to cell therapy comprising administering to the affected subject a therapeutically effective amount of the cells of the invention.

In one embodiment, the cells are obtained and cultured as described herein in order to derive and store the cells for therapeutic uses using cell therapy should the subject require, for example, disease therapy, tissue repair, transplantation, treatment of a cellular debilitation, or treatment of cellular dysfunctions in the future.

In another embodiment of the invention, cells derived from a subject are directly differentiated in vitro or in vivo to generate differentiating or differentiated cells without generating a cell line. These cells are useful in medical and biological research and in the treatment of disease by providing cells for use in cell therapy, e.g., allogeneic cell therapy.

The adipose tissue stem cells and adipose tissue-derived cells generated by the above-mentioned techniques are utilized in research relating to cell biology, drug discovery, and in cell therapy, including but not limited to production of cells for the treatment of various diseases, disorders, and conditions, in addition to wound healing. In one aspect, they are useful in enhancing wound healing in diabetic patients. They are also useful for treating other wounds and injuries, as well as diseases, disorders, and conditions such as burns, skin aging, in addition to the uses for diabetic wound healing described herein.

Such cell therapy methods encompass the use of the cells of this invention in combination with growth factors or chemokines such as those inducting proliferation, lineage-commitment, or genes or proteins of interest. Treatment methods may include providing stem or appropriate precursor cells directly for transplantation where the tissue is regenerated in vivo or recreating the desired tissue in vitro and then providing the tissue to the affected subject.

The composites and/or cells of the present invention can be used as a vehicle for the in situ delivery of biologically active agents. The biologically active agents incorporated into, or included as an additive within, the composite of the subject invention can include, without limitation, medicaments, growth factors, vitamins, mineral supplements, substances used for the treatment, prevention, diagnosis, cure or mitigation of disease or illness, substances which affect the structure or function of the body, or drugs. The biologically active agents can be used, for example, to facilitate implantation of the composite or cell suspension into a subject to promote subsequent integration and healing processes. The active agents include, but are not limited to, antifungal agents, antibacterial agents, anti-viral agents, anti-parasitic agents, growth factors, angiogenic factors, anesthetics, mucopolysaccharides, metals, cells, and other wound healing agents. Because the processing conditions can be relatively benign (physiological temperature and pH), live cells can be incorporated into the composite during its formation, or subsequently allowed to infiltrate the composite through tissue engineering techniques.

Chronic wounds are wounds characterized by non-healing skin wounds and include chronic venous ulcers, diabetic ulcers, arterial ulcers, pressure ulcers (e.g., decubitis ulcers), radiation ulcers, traumatic wounds, and open, complicated non-healing wounds.

According to an embodiment, a formulation of the invention contains an antimicrobial agent. The antimicrobial agent may be provided at, for example, a standard therapeutically effective amount. A standard therapeutically effective amount is an amount that is typically used by one of ordinary skill in the art or an amount approved by a regulatory agency (e.g., the FDA or its European counterpart).

In another embodiment, a formulation of the invention can be impregnated into a dressing material (or otherwise contained or encompassed by the dressing material). The dressing material is a pharmaceutically acceptable fabric. It can be, for example, gauze or any other type of medical fabric or material that can be used to cover a wound and/or to keep a therapeutic agent or composition in contact with a patient.

The composition of the invention can further comprise additional therapeutic additives, alone or in combination (e.g., 2, 3, or 4 additional additives). Examples of additional additives include but are not limited to: (a) antimicrobials, (b) steroids (e.g., hydrocortisone, triamcinolone); (c) pain medications (e.g., aspirin, an NSAID, and a local anesthetic); (d) anti-inflammatory agents; and (e) combinations thereof.

The present invention provides methods for administering ASCs and their progeny to subjects in need thereof. In one aspect, the ASCs have been pretreated to differentiate into a precursor cell of interest or into a fully differentiated state. In another aspect, populations of ASCs can be treated with more than one type of differentiation inducing agent or medium, or a combination of agents, which induce more than one type of differentiation. In another aspect, separate populations of ASCs, that have been pretreated with cell differentiation-inducing compounds, or no treatment at all, can be co-administered to a subject. Co-administration of different groups of cells does not necessarily mean that the ASC populations are actually administered at the same time or that the populations are combined or administered in the same composition. The invention further provides compositions and methods for administering ASCs to subjects and then inducing the ASCs to differentiate in vivo by also administering cell differentiation-inducing agents to the subject. In one aspect, the subject is a human. When more than one differentiation agent or compound is used to induce cells along a particular cell pathway, or when additional agents are also used to induce some of the cells to differentiate along a second pathway, the various agents need not be provided at the same time. Various compounds and growth factors can be used with the cells of the invention to induce or modulate differentiation or maturation.

The cells of the present invention may be administered to a subject alone or in admixture with a composition useful in the repair of tissue, bone, and vascular injury and defects. Such compositions include, but are not limited to bone morphogenetic proteins, hydroxyapatite/tricalcium phosphate particles (HA/TCP), gelatin, poly-L-lysine, and collagen.

Non-synthetic matrix proteins like collagen, glycosaminoglycans, and hyaluronic acid, which are enzymatically digested in the body, are useful for delivery (see U.S. Pat. Nos. 4,394,320; 4,472,840; 5,366,509; 5,606,019; 5,645,591; and 5,683,459) and are suitable for use with the present invention. Other implantable media and devices can be used for delivery of the cells of the invention in vivo. These include, but are not limited to, sponges, such as those from Integra, fibrin gels, scaffolds formed from sintered microspheres of polylactic acid glycolic acid copolymers (PLAGA), and nanofibers formed from native collagen, as well as other proteins. The cells of the present invention can be further combined with growth factors, nutrient factors, pharmaceuticals, calcium-containing compounds, anti-inflammatory agents, antimicrobial agents, or any other substance capable of expediting or facilitating bone or tissue growth, stability, and remodeling.

The compositions of the present invention can also be combined with inorganic fillers or particles. For example for use in implantable grafts the inorganic fillers or particles can be selected from hydroxyapatite, tri-calcium phosphate, ceramic glass, amorphous calcium phosphate, porous ceramic particles or powders, mesh titanium or titanium alloy, or particulate titanium or titanium alloy.

In one embodiment, a composition comprising the cells of the invention is administered locally by injection. Compositions comprising the cells can be further combined with known drugs, and in one embodiment, the drugs are bound to the cells. These compositions can be prepared in the form of an implantable device that can be molded to a desired shape. In one embodiment, a graft construct is prepared comprising a biocompatible matrix and one or more cells of the present invention, wherein the matrix is formed in a shape to fill a gap or space created by the removal of a tumor, injured, or diseased tissue.

The cells can be seeded onto the desired site within the tissue to establish a population. Cells can be transferred to sites in vivo using devices such as catheters, trocars, cannulae, stents (which can be seeded with the cells), etc.

The cells can be employed alone or within biologically-compatible compositions to generate differentiated tissues and structures, both in vivo and in vitro, or to stimulate a process of interest in a tissue. Additionally, the cells can be expanded and cultured to produce hormones, growth factors, including pleiotropic growth factors, cytokines, and chemokines, and to provide conditioned culture media for supporting the growth and expansion of other cell populations. In another aspect, the invention encompasses a lipo-derived lattice substantially devoid of cells, which includes extracellular matrix material form adipose tissue. The lattice can be used as a substrate to facilitate the growth and differentiation of cells, whether in vivo or in vitro, into anlagen or mature tissue or structures, as well as to provide an environment which maintains the viability of the cells.

The present invention thus provides methods and compositions for delivering incredibly large numbers of ASCs, precursors, or differentiated cells derived from adipose tissue for the procedures and treatments described herein. Additionally, for diseases that require cell infusions or administration, adipose tissue harvest is minimally invasive, yields many cells, and can be done repeatedly The present invention encompasses the preparation and use of immortalized cell lines, including, but not limited to, adipose tissue-derived cell lines capable of differentiating into at least one cell type. Various techniques for preparing immortalized cell lines are known to those of ordinary skill in the art.

The present invention also encompasses the preparation and use of cell lines or cultures for testing or identifying agents for their effects on adipose tissue or bone. The present invention further encompasses compounds, which are identified using any of the methods described herein. Such compounds may be formulated and administered to a subject for treatment of the diseases, disorders, conditions, and injuries disclosed herein.

In one embodiment, genes of interest can be introduced into cells of the invention. In one aspect, such cells can be administered to a subject. In one aspect, the subject is afflicted with a disease, disorder, condition, or injury. In one aspect, the cells are modified to express exogenous genes or are modified to repress the expression of endogenous genes, and the invention provides a method of genetically modifying such cells and populations. In accordance with this method, the cell is exposed to a gene transfer vector comprising a nucleic acid including a transgene, such that the nucleic acid is introduced into the cell under conditions appropriate for the transgene to be expressed within the cell. The transgene generally is an expression cassette, including a coding polynucleotide operably linked to a suitable promoter. The coding polynucleotide can encode a protein, or it can encode biologically active RNA (e.g., antisense RNA or a ribozyme). Thus, for example, the coding polynucleotide can encode a gene conferring resistance to a toxin, a hormone (such as peptide growth hormones, hormone releasing factors, sex hormones, adrenocorticotrophic hormones, cytokines (e.g., interferons, interleukins, lymphokines), a cell-surface-bound intracellular signaling moiety (e.g., cell adhesion molecules, hormone receptors), a factor promoting a given lineage of differentiation, etc.

In addition to serving as useful targets for genetic modification, many cells and populations of the present invention secrete various polypeptides. Such cells can be employed as bioreactors to provide a ready source of a given hormone, and the invention pertains to a method of obtaining polypeptides from such cells. In accordance with the method, the cells are cultured under suitable conditions for them to secrete the polypeptide into the culture medium. After a suitable period of time, and preferably periodically, the medium is harvested and processed to isolate the polypeptide from the medium. Any standard method (e.g., gel or affinity chromatography, dialysis, lyophilization, etc.) can be used to purify the hormone from the medium, many of which are known in the art.

In other embodiments, cells (and populations) of the present invention secreting polypeptides can be employed as therapeutic agents. Generally, such methods involve transferring the cells to desired tissue, either in vitro or in vivo, to animal tissue directly. The cells can be transferred to the desired tissue by any method appropriate, which generally will vary according to the tissue type.

Compositions comprising cells of the invention can be employed in any suitable manner to facilitate the growth and differentiation of the desired tissue. For example, the composition can be constructed using three-dimensional or stereotactic modeling techniques. To direct the growth and differentiation of the desired structure, the composition can be cultured ex vivo in a bioreactor or incubator, as appropriate. In other embodiments, the structure is implanted within the host animal directly at the site in which it is desired to grow the tissue or structure. In still another embodiment, the composition can be engrafted onto a host, where it will grow and mature until ready for use. Thereafter, the mature structure (or anlage) is excised from the host and implanted into the host, as appropriate.

Matrices suitable for inclusion into the composition can be derived from various sources. As discussed above, the cells, matrices, and compositions of the invention can be used in tissue engineering and regeneration. Thus, the invention pertains to an implantable structure (i.e., an implant) incorporating any of these inventive features. The exact nature of the implant will vary according to the intended use. The implant can be, or comprise, as described, mature or immature tissue. Thus, for example, one type of implant can be a bone implant, comprising a population of the inventive cells that are undergoing (or are primed for) adipose, chondrogenic, or osteoclastic differentiation, optionally seeded within a matrix material. Such an implant can be applied or engrafted to encourage the generation or regeneration of mature bone or other tissue within the subject.

One of ordinary skill in the art would appreciate that there are other carriers useful for delivering the cells of the invention. Such carriers include, but are not limited to, calcium phosphate, hydroxyapatite, and synthetic or natural polymers such as collagen or collagen fragments in soluble or aggregated forms. In one aspect, such carriers serve to deliver the cells to a location or to several locations. In another aspect, the carriers and cells can be delivered either through systemic administration or by implantation. Implantation can be into one site or into several sites.

As indicated above, cells can be seeded onto and/or within the organic/inorganic composites of the present invention. Likewise, tissues such as cartilage can be associated with the composites prior to implantation within a patient. Examples of such cells include, but are not limited to, bone cells (such as osteoclasts, osteoblasts, and osteocytes), blood cells, epithelial cells, neural cells (e.g., neurons, astrocytes, and oligodendrocytes), and dental cells (odontoblasts and ameloblasts). Seeded cells can be autogenic, allogenic, or xenogeneic. Seeded cells can be encapsulated or non-encapsulated.

Examples of antimicrobial agents that can be used in the present invention include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, cikprofloxacin, doxycycline, ampicillin, amphotericine B, ketoconazole, fluconazole, pyrimethamine, sulfadiazine, clindamycin, lincomycin, pentamidine, atovaquone, paromomycin, diclarazaril, acyclovir, trifluorouridine, foscarnet, penicillin, gentamicin, ganciclovir, iatroconazole, miconazole, Zn-pyrithione, and silver salts, such as chloride, bromide, iodide, and periodate.

Growth factors that can be incorporated into the composite of the present invention include, but are not limited to, bone growth factors (e.g., BMP, OP-1), basic fibroblast growth factor (bFGF), acidic fibroblast growth factor (aFGF), nerve growth factor (NGF), epidermal growth factor (EGF), insulin-like growth factors 1 and 2 (IGF-1 and IGF-2), platelet-derived growth factor (PDGF), tumor angiogenesis factor (TAF), vascular endothelial growth factor (VEGF), corticotropin releasing factor (CRF), transforming growth factors alpha and beta (TGF-.alpha. and TGF-.beta.), interleukin-8 (IL-8), granulocyte-macrophage colony stimulating factor (GM-CSF), the interleukins, and the interferons.

Other agents or compounds that can be incorporated into the composite of the subject invention include acid mucopolysaccharides including, but not limited to, heparin, heparin sulfate, heparinoids, dermatan sulfate, pentosan polysulfate, chondroitin sulfate, hyaluronic acid, cellulose, agarose, chitin, dextran, carrageenin, linoleic acid, and allantoin.

Proteins and other biologically active compounds that can be incorporated into, or included as an additive within, a composition comprising cells of the present invention include, but are not limited to, collagen (including cross-linked collagen), fibronectin, laminin, elastin (including cross-linked elastin), osteopontin, osteonectin, bone sialoproteins (Bsp), alpha-2HS-glycoproteins, bone Gla-protein (Bgp), matrix Gla-protein, bone phosphoglycoprotein, bone phosphoprotein, bone proteoglycan, protolipids, bone morphogenetic protein, cartilage induction factor, platelet derived growth factor and skeletal growth factor, enzymes, or combinations and biologically active fragments thereof. Other proteins associated with other parts of human or other mammalian anatomy can be incorporated or included as an additive, include proteins associated with cartilage, such as chondrocalcining protein, proteins associated with dentin, such as phosphoryin, glycoproteins and other Gla proteins, or proteins associated with enamel, such as amelogenin and enamelin. Agents incorporated into the composition of the present invention may or may not facilitate or enhance osteoinduction. Adjuvants that diminish an immune response can also be used in conjunction with the composite of the subject invention.

In one embodiment, the biologically active agents or compounds can first be encapsulated into microcapsules, microspheres, microparticles, microfibers, reinforcing fibers and the like to facilitate mixing and achieving controlled, extended, delayed and/or sustained release and combined with the cells of the invention. Encapsulating the biologically active agent can also protect the agent against degradation during formation of the composite of the invention.

In a preferred embodiment of the invention, the biologically active agent is controllably released into a subject when the composition of the invention is implanted into a subject, due to bioresorption relying on the time scale resulting from cellular remodeling. In one aspect, the composition may be used to replace an area of discontinuity in the tissue. The area of discontinuity can be the result of trauma, a disease, disorder, or condition, surgery, injury, etc.

Antibodies may be generated using methods that are well known in the art. For instance, U.S. patent application Ser. No. 07/481,491, which is incorporated by reference herein in its entirety, discloses methods of raising antibodies to specific proteins. For the production of antibodies, various host animals, including but not limited to rabbits, mice, and rats, can be immunized by injection with a specific polypeptide or peptide fragment thereof. To increase the immunological response, various adjuvants may be used depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

For the preparation of monoclonal antibodies, any technique which provides for the production of antibody molecules by continuous cell lines in culture may be utilized. For example, the hybridoma technique originally developed by Kohler and Milstein (1975, *Nature* 256:495-497), the trioma technique, the human B-cell hybridoma technique (Kozbor et al., 1983, *Immunology Today* 4:72), and the EBV-hybridoma technique (Cole et al., 1985, in *Monoclonal Antibodies and Cancer Therapy*, Alan R. Liss, Inc., pp. 77-96) may be employed to produce human monoclonal antibodies. In another embodiment, monoclonal antibodies are produced in germ-free animals utilizing the technology described in international application no. PCT/US90/02545, which is incorporated by reference herein in its entirety.

In accordance with the invention, human antibodies may be used and obtained by utilizing human hybridomas (Cote et al., 1983, *Proc. Natl. Acad. Sci. U.S.A.* 80:2026-2030) or by transforming human B cells with EBV virus in vitro (Cole et al., 1985, in *Monoclonal Antibodies and Cancer Therapy*, Alan R. Liss, Inc., pp. 77-96). Furthermore, techniques developed for the production of "chimeric antibodies" (Morrison et al., 1984, *Proc. Natl. Acad. Sci. U.S.A.* 81:6851-6855; Neuberger et al., 1984, *Nature* 312:604-608; Takeda et al., 1985, *Nature* 314:452-454) by splicing the genes from a mouse antibody molecule specific for epitopes of SLLP polypeptides together with genes from a human antibody molecule of appropriate biological activity can be employed; such antibodies are within the scope of the present invention. Once specific monoclonal antibodies have been developed, the preparation of mutants and variants thereof by conventional techniques is also available.

In one embodiment, techniques described for the production of single-chain antibodies (U.S. Pat. No. 4,946,778, incorporated by reference herein in its entirety) are adapted to produce protein-specific single-chain antibodies. In another embodiment, the techniques described for the construction of Fab expression libraries (Huse et al., 1989, *Science* 246:1275-1281) are utilized to allow rapid and easy identification of monoclonal Fab fragments possessing the desired specificity for specific antigens, proteins, derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment; the Fab fragments which can be generated by treating the antibody molecule with papain and a reducing agent; and Fv fragments.

The generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

A nucleic acid encoding the monoclonal antibody obtained using the procedures described herein may be cloned and sequenced using technology which is available in the art, and is described, for example, in Wright et al. (1992, Critical Rev. in Immunol. 12(3,4):125-168) and the references cited therein. Further, the antibody of the invention may be "humanized" using the technology described in Wright et al., (supra) and in the references cited therein, and in Gu et al. (1997, Thrombosis and Hematocyst 77:4:755-759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al., (supra).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222: 581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

In the production of antibodies, screening for the desired antibody can be accomplished by techniques known in the art, e.g., ELISA (enzyme-linked immunosorbent assay). Antibodies generated in accordance with the present invention may include, but are not limited to, polyclonal, monoclonal, chimeric (i.e., "humanized"), and single chain (recombinant) antibodies, Fab fragments, and fragments produced by a Fab expression library.

The peptides of the present invention may be readily prepared by standard, well-established techniques, such as solid-phase peptide synthesis (SPPS) as described by Stewart et al. in Solid Phase Peptide Synthesis, 2nd Edition, 1984, Pierce Chemical Company, Rockford, Ill.; and as described by Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenyl esters.

Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl-blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high-resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, C8- or C18-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

It will be appreciated, of course, that the peptides or antibodies, derivatives, or fragments thereof may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tartaric, citric, benzoic, cinnamie, mandelic, methanesulfonic, ethanesulfonic, p-toluenesulfonic, salicyclic and the like, to provide a water soluble salt of the peptide is suitable for use in the invention.

The present invention also provides for analogs of proteins. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. To that end, 10 or more conservative amino acid changes typically have no effect on peptide function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides or antibody fragments which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

The invention also includes a kit comprising the composition of the invention and an instructional material which describes administering or using the composition. In another embodiment, this kit comprises a (preferably sterile) solvent suitable for dissolving or suspending the composition of the invention prior to administering the composition. Optionally, at least one growth factor and/or antimicrobial agent may be included in the kit.

As used herein, an "instructional material" includes a publication, a recording, a diagram, or any other medium of expression which can be used to communicate the usefulness of the invention in the kit for effecting enrichment and growth of adipose stem cells. Optionally, or alternately, the instructional material may describe one or more methods of alleviation the diseases or disorders in a cell or a tissue of a mammal. The instructional material of the kit of the invention may, for example, be affixed to a container which contains the compositions of the invention or be shipped together with a container which contains the antibody. Alternatively, the instructional material may be shipped separately from the container with the intention that the instructional material and the compound be used cooperatively by the recipient.

EXAMPLES

Example 1

General Methods

The adipose tissue-derived stromal cells useful in the methods of invention are isolated by a variety of methods known to those of ordinary skill in the art. A preferred source of adipose tissue is subcutaneous adipose. In humans, the adipose is typically isolated by liposuction.

Human adipose tissue-derived adult stromal cells represent a stem cell source that can be harvested routinely with minimal risk or discomfort to the patient. They can be expanded ex vivo, differentiated along unique lineage pathways, genetically engineered, and re-introduced into individuals as either autologous or allogeneic transplantation.

Methods for the isolation, expansion, and differentiation of human adipose tissue-derived cells have been reported. See for example, Burris et al 1999, Mol Endocrinol 13:410-7; Erickson et al 2002, Biochem Biophys Res Commun. Jan. 18, 2002; 290(2):763-9; Gronthos et al 2001, Journal of Cellular Physiology, 189:54-63; Halvorsen et al 2001, Metabolism 50:407-413; Halvorsen et al 2001, Tissue Eng. 7(6):729-41; Harp et al 2001, Biochem Biophys Res Commun 281:907-912; Saladin et al 1999, Cell Growth & Diff 10:43-48; Sen et al 2001, Journal of Cellular Biochemistry 81:312-319; Zhou et al 1999, Biotechnol. Techniques 13: 513-517. Adipose tissue-derived stromal cells are obtained from minced human adipose tissue by collagenase digestion and differential centrifugation (Halvorsen et al 2001, Metabolism 50:407-413; Hauner et al 1989, J Clin Invest 84:1663-1670; Rodbell et al 1966, J. Biol. Chem. 241:130-139). Others have demonstrated that human adipose tissue-derived stromal cells can differentiate along the adipocyte, chondrocyte, and osteoblast lineage pathways (Erickson et al 2002, Biochem Biophys Res Commun. Jan. 18, 2002; 290(2):763-9; Gronthos et al 2001, Journal of Cellular Physiology, 189:54-63; Halvorsen et al 2001, Metabolism 50:407-413; Halvorsen et al, 2001, Tissue Eng. Dec. 7, 2001; (6):729-41; Harp et al 2001, Biochem Biophys Res Commun 281:907-912; Saladin et al 1999, Cell Growth & Diff 10:43-48; Sen et al 2001, Journal of Cellular Biochemistry 81:312-319; Zhou et al 1999, Biotechnol. Techniques 13: 513-517; Zuk et al 2001, Tissue Eng. 7: 211-228).

WO 00/53795, WO 2007/030652, and WO 2007/019107 provide methods for obtaining and culturing ASCs.

Adipose Stem Cell Isolation and Culture

For these studies, subcutaneous adipose tissue was obtained from patients undergoing elective surgical procedures. Discarded excisional abdominoplasty specimens and/or liposuction aspirates from over 40 patients (average age 42.4 years, range 24-70 years; average BMI of 30.14, range of 18.4-63.6) were processed as described previously. Excisional specimens were liposuctioned under sterile laboratory conditions. All specimens were generously washed with Hanks balanced salt solution with calcium and magnesium. The rinsed aspirate was then digested in Liberase Blendzyme 1 (Roche 1 988 417, 9 mg/ml) for 30-60 minutes until a smooth and even consistency was obtained. The cellular pellet was isolated via centrifugation, filtered through 250 µm nylon mesh, washed with erythrocyte lysis buffer, refiltered through 105 µm nylon mesh, and the resulting cell suspension was cultured at 37° C., 5% $CO_2$ in one of the following medias:

1. "D-10": DMEM/F12 (Gibco Cat No. 11320-033) with 10% Fetal Bovine Serum and 1% antibiotic/antimycotic (ABAM, Gibco Cat No. 15240-062) supplement.

2. "AR8": a novel chemically-defined, serum-free medium developed in the Katz lab. It consists of DMEM/F12, 1% ABAM, 0.1 mM L-glutamine (Gibco Cat No. 25030-081), 0.50% ITS+3 (Sigma 1-2771), 0.05% Fatty Acid Supplement (Sigma F-7050), 1% MEM non-essential amino acids (Gibco Cat No. 11140-050), 100 µM ascorbic acid 2-phosphate (Sigma A-8960), 1 ng/ml PDGF-BB (Research Diagnostics Inc RDI-114b), 10 ng/ml EGF (R & D Systems 236EG), 1 ng/ml SCGF-b (Research Diagnostics Inc RDI-1022B), 1 ng/ml TNFα (Research Diagnostics Inc RDI-301), 1 ng/ml IL-1b (Research Diagnostics Inc RDI-201B), $1\times10^{-8}$ M beta-estradiol (Sigma E2758-1G), $1\times10^{-8}$ M progesterone (Sigma P8783-5G), $1\times10^{-8}$M dexamethasone (Sigma D-8893), and 500 ng/ml hydrocortisone (Sigma H0888-1G).

3. "AR8-1% HS": The AR8 base medium with 1% human serum (CaSNiMrex 14-402E).

4. "1:10 AR8": The AR8 base medium diluted 1:10 in DMEM/F12 with 1% ABAM.

5. "1:10 AR8-1% HS": The above diluted AR8 medium with 1% human serum.

6. "D-0": DMEM/F12 with 1% ABAM and NO other additives.

Freshly isolated cells were plated into monolayer culture in traditional culture-ware (Nunclon 100 dia.×15 mm H). The initial plating was designated as "passage 0" ($P^0$). At confluence, $P^0$ cells were lifted using the fungal derived enzyme TrypLE (Gibco Cat No. 12604-013) and counted on a hemocytometer using trypan blue exclusion. Cells were then used for study or re-plated at 2,000 cells/cm² for continued expansion. In all studies described, ASCs from passage 5 or less were used. For some studies, ASCs were fluorescently labeled with DiI or DiO (Molecular Probes) per manufacturer's instructions. Briefly, cells were rinsed to remove serum, if present, and incubated in 1:200 representative dye solution in serum-free medium for 15 minutes at 37° C., and subsequently rinsed again to remove excess dye.

Formation of ASC Aggregates (i.e., SOM-Bs, Self-Organizing Niche Milieus, or ASC "SNiMs"):

These ASC aggregates referred to as SNiMs, are also referred to as SOM-B, aggregates, spheres, and mesenchoid bodies. ASCs reproducibly form cell aggregates. ASCs (500-50,000) were suspended in the appropriate medium to achieve desired concentrations. Small volumes (15-30 µl) of the cell solution were then pipetted onto the inner surface of a culture plate cover in discrete drops. The culture plate covers were then flipped upside down (now actually right-side up) to result in "hanging droplets". The plates were placed in humid chambers to prevent media from drying out and the droplets maintained in standard tissue culture incubators for 24-72 hours. During this time, the cells coalesced into an aggregate(s) at the most dependent part of the hanging drop. Our lab refers to these aggregates as "self-organizing niche milieus", or "SNiMs". After 24-72 hours in hanging drop culture, the SNiMs were then transferred into either Ultra Low Attachment (ULA) wells/plates (Corning) for suspension culture, or into standard cultureware for adherent culture. In some experiments, ASC-SNiMs were labeled with Hoechst 33342 (Molecular Probes Cat. #H1399) to reveal distribution of cell nuclei. ASC-SNiMs were rinsed with PBS and incubated in 4 mM dye solution for 15 min in the dark at 37° C. ASC-SNiMs were subsequently rinsed with PBS and placed in appropriate medium.

Compromised wound healing seen in diabetic patients has long been recognized as the main contributing factor for clinical outcomes ranging from chronic skin ulcers to foot amputations. Defects including dysfunctional native stem cells and inflammatory cytokine dysregulation have been proposed as possible mechanisms behind this frequently debilitated clinical condition. In an effort to learn whether adipose stem cells (ASCs) might help to overcome this tissue compromise we investigated the effects ASCs applied topically to 1 cm full thickness dorsal biopsy wounds on db/db mice. Preliminary results with one cell line found an initial therapeutic response in which cell treated animals healed nearly one week sooner than controls. In follow-up studies testing three distinct patient cell lines, wounds reached 75% closure by 8.69 days with one patient line compared with 11.56 days for control diabetic mice (p=0.024). This treatment came close to restoring wound healing to those seen in nondiabetic controls (7.17 days; p=0.755). Repeated measures ANOVA confirmed the therapeutic effect of this particular cell line over time (p=0.03) but failed to find a significant effect associated with the two additional cell lines investigated.

Further examined was the potential of adipose derived stem cells applied on the first post operative day to improve the healing rates of dorsal wounds in db/db mice. In preliminary trials, wound area measured as a percent of original area was reduced to 8% in cell treated mice as compared to 51% in untreated mice by postop day 12 (p<0.001). The efficacy of human cells, despite transplant into an immuno-competent murine model, may indicate a reduced or absent role played by rejection, and perhaps suggest the potential for the development of off-the-shelf allogenic sources of stem cells for topical use.

Common Experimental Design

Cells were cultured for 2-3 passages in DMEM/F12+10% FBS+1% ABAM (antibiotic antimycotic), we tested both single cell suspensions as well as cell clusters. Single cell suspension-cells were trypsinized, washed in sterile PBS, and suspended in 200 µl PBS. ASC clusters (SOM-Bs)-cells were plated at 2.5-5.66×10⁵ cells/well in 24-well ultra low attachment plates, the cells were allowed to coalesce into cell clusters over 48 hours, they were then collected, washed in sterile PBS, and suspended in 200 µl PBS. Alternatively, ASC SOM-Bs were prepared using the hanging drop method described above.

Male db/db diabetic mice and db/-nondiabetic littermate controls mice were obtained from Jackson labs (Stock Number 000642). The mice were housed until their blood glucose >250 mg/dL.

For surgical procedures, mice were anesthetized, clipped, depillated, and prepped with betadine. 1 cm full thickness dorsal skin biopsy wounds were made on each mouse. Wounds were photographed using a digital camera. Wounds were dressed with Tegaderm and benzoin.

To administer the cells, 1.2-1.4 million cells were applied topically to each wound on postop day 1 (the cells were injected beneath a Tegaderm, translucent impermeable dressing, but not into the tissue itself). For control animals, 200 ul sterile PBS was injected To measure the size of wounds, the wounds were serially photographed over the following 3-4 weeks. Wound area was calculated using the NIH image processing program ImageJ.

Cells were also characterized as to detectable cell-surface markers (Table 1).

TABLE 1

Cell Surface Markers
Table 1: Cell surface characterization of ASCs Used in Wound Healing Trial III.

| Surface Marker | Positive Cells (%) | | |
|---|---|---|---|
| | PATIENT A H6-08L (P = 3) | PATIENT B H6-09L (P = 2) | PATIENT C H6-10L (P = 2) |
| HLA-ABC PE | 99.35 | 99.45 | 99.35 |
| NG2 PE | 33.65 | 33.30 | 27.19 |
| CD34 (8G12) PE | 8.33 | 23.37 | 14.42 |
| ALDH | 24.70 | 25.68 | 11.92 |

ASCs were characterized using flow cytometry in parallel to their use in diabetic wounds. Patient B ASCs demonstrated significantly enhanced healing in vivo, as well as a higher percentage of CD34+ cells compared to the other two cell preps.

Example 2

Production of Growth Factors by SOMBs (SNiMs)

Materials and Methods:
Growth Factor Studies:

To determine whether ASC-SOM-Bs (SNiMs) produce growth factors when maintained in suspension culture, freshly isolated ASCs were grown to confluence in adherent monolayer culture in D10 medium. The cells were lifted into suspension and depleted of CD31+ and CD45+ cells using MACS columns (Miltenyi Biotech Cat #130-042-201) and anti-CD 31PE and anti-CD 45PE antibodies (BD Bioscience) and anti-PE microbeads (Miltenyi Biotech, #130-048-801). The passage 1 (P¹) CD31−/CD45− ASCs were then plated into monolayer culture at 2000 cells/cm² in D10 medium. At confluence, the cells were again lifted into suspension and an aliquot was used for immuno-characterization using flow cytometry (see below). Of the remaining cells, half were used to create 20,000 cell SOM-Bs (SNiMs), and the other half were kept in monolayer culture. After 24-48 hours in hanging drop, individual SOM-Bs (SNiMs) were transferred to suspension culture in 6 well ULA plates (Day 0) and maintained in one of 4 culture mediums: D0, D10, 1:10 AR8, or 1:10 AR8-1% HS. For comparison, monolayer-cultured ASCs were (re)plated at 2,000 cells/cm² into adherent monolayer culture using the same media conditions (Day 0). Cell culture supernatant was then collected (and fresh medium replaced) from each culture condition on post-plating day 3, 6, and 10. The supernatant from each of 6 wells was combined and frozen for subsequent quantitative ELISA analysis of growth factor levels. Each sample (representing the combined supernatants from 6 separate but identical cultures) was analyzed in duplicate by Pierce Biotechnology's Searchlight™ service, using appropriate standard curves for each analyte.

Flow Cytometry:

To delineate the immunophenotype of ASCs used to fabricate SOM-Bs (SNiMs) we performed flow cytometric analysis of various cell surface markers. Flow cytometry was performed on a Becton Dickinson FACS Calibur with 488 nm argon-ion lasers and 635 nm diode laser for excitation and fluorescence emission was collected using 530/30 nm (FL1), 585/42 nm (FL2) bandpass filters, 670 nm (FL3) long pass filter and 661/16 nm (FL4) bandpass using logarithmic amplification. Cells were released with TrypLE Express and resuspended in DMEMJF12+10% FBS. The cells were then centrifuged and re-suspended in wash flow buffer at a concentration of $1\times10^6$ cells/ml. Wash flow buffer consisted of phosphate buffer supplemented with 2% (v/v) FBS (Invitrogen) and 0.1% (w/v) sodium azide, $NaN_3$ (Sigma). Cell viability was >98% by Trypan Blue dye (GIBCO) exclusion technique. 250,000 cells were stained with saturating concentrations of phycoerythrin-(PE) and allophycocyanin (APC) or Alexa Fluor 647 conjugated antibodies and isotype matched controls. The cells were incubated in the dark for 30 min at 4° C. After incubation, cells were washed three times with wash flow buffer and re-suspended in 0.25 ml of cold protein-free PBS. Ten minutes before analysis 20 µl 7-Amino-Actinomycin D(7AAD)(VIA-PROBE™ BD Biosciences) was added into PBS buffer to label dead cells.

Flow cytometer instrument settings were set using unstained cells. Cells were gated by forward vs. side scatter to eliminate debris. Because highly autofluorescent cells can overlap with cells expressing low levels of an antigen, the sensitivity of the fluorescence signal was increased by eliminating the autofluorescence signal out of the FL1 channel and thereby removing the contribution of autofluorescence in the measurement channel. The dead cells were gated out with 7AAD by FL3 channel. A positive fluorescence was established to use a same fluorescence conjugated isotype-matched control. A minimum of 10,000 events were counted for each analysis. ASCs were stained with the following antibodies: anti-human CD31, CD34 (clone 8G12), and CD146 from BD Biosciences; anti-human CD184 (CXCR4) from eBioscience; anti-human CD271 from Miltenyi Biotech; Stro-1 from R&D Systems; NG2, and goat anti-mouse Alex Fluor647 from Molecular Probes.

Results

I. ASCs Organize into 3-Dimensional Multicellular Aggregates (ASC-SOM-Bs (SNiMs)) in a Controlled, Reproducible Fashion.

Using a hanging drop culture technique, we demonstrate the successful and reproducible formation of ASC spheroids (ASC-SOM-Bs (SNiMs)) using varied numbers (ranging from 500 to 50,000) of early passage ASCs isolated and cultured from multiple donors. The SOM-Bs (SNiMs) form in a range of media volumes (15-30 microliters) as well as in a variety of media types, including DMEM/F12 with 10% FBS (D-10), DMEM/F12 without serum or additives (D-0), serum-free ASC medium (AR8 and 1:10 AR8), or low serum ASC medium (AR8-1% HS; 1:10 AR8-1% HS). Using the hanging drop method, ASCs typically organize into discrete spheroids within 24-72 hours and can be reliably transferred to suspension or adherent culture conditions thereafter without damage to, or loss of form. Multiple and variably sized cell aggregates form in hanging drops when fewer than 2000 ASCs are used for spheroid formation, and/or depending on the time spent in hanging drop. In contrast, large, single SOM-Bs (SNiMs) of consistent size form at high efficiency when larger numbers of cells are used (~5,000 and higher). See also PCT/US2007/002572.

II. ASC-SOM-Bs (SNiMs) can be Maintained for Prolonged Periods in Suspension Culture and Display Robust Survival Capacity when Grown in Various Serum-Free Culture Conditions.

Figure 8:
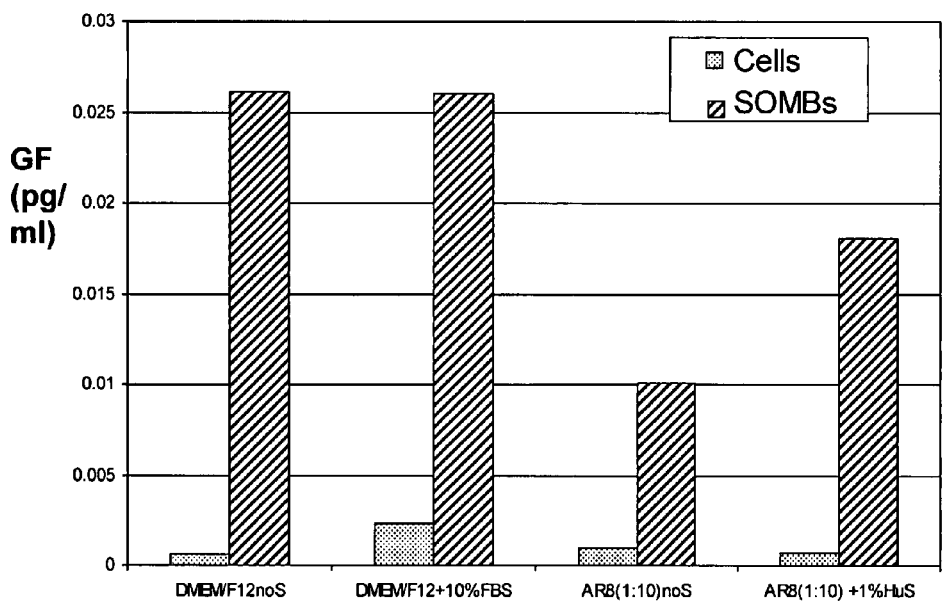
FIG. 8 is a depiction of a bar graph illustrating production of human Hepatocyte Growth Factor (hHGF) by human ASCs maintained in different culture conditions (Day 3). Equal numbers of human ASCs were plated into monolayer culture or formed in parallel into SNiMs and placed in suspension culture (Day 0). The cells/SNiMs were cultured in one of four mediums: DMEM/F12 with no other additives except antibiotics (D0); DMEM/F12 with 10% FBS (D10); chemically defined serum-free medium with growth factor additives (AR8(1:10)noS); and low serum medium (AR8(1:10) with 1% human serum (HS). On day 3, culture supernatant was collected and analyzed by ELISA for growth factor levels. Each sample was tested in duplicate at multiple dilutions, and represents the combined average of 6 separate samples. Bars-Cells (stippled); SOMBS (diagonal cross hatching).
Figure 9:
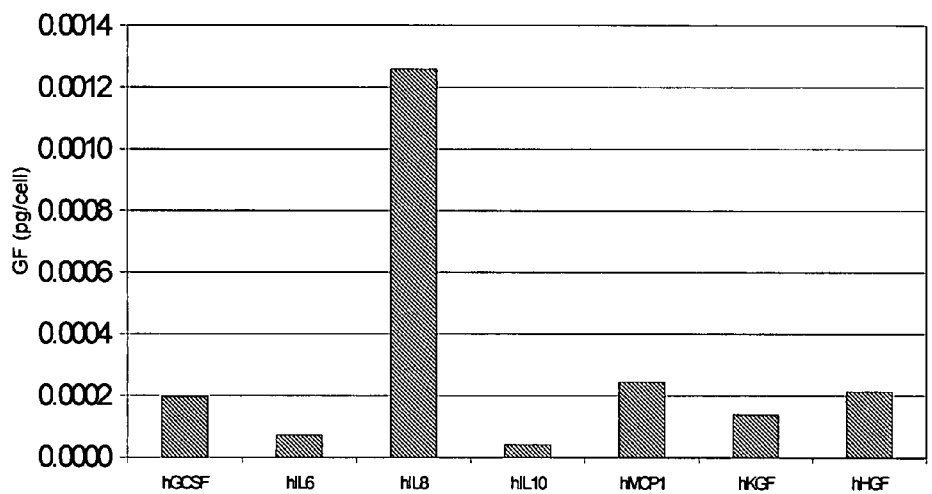
FIG. 9 graphically illustrates the growth factor (gf) production by suspension cultured human ASC SNiMs maintained in unfortified medium (Day 10). After hanging drop culture for 2 days, human ASC SNiMs were placed into suspension culture and maintained for 10 days in D0 medium (i.e., no serum, no growth factor additives). Media was replaced on days 3, 6 and 10. On day 10, supernatant was collected for ELISA analysis and SNiMs were dissociated to determine cell numbers. Each growth factor (hGCSF, hIL6, hIL8, hIL10, hMCP1, hKGF, and hHGF) was tested in duplicate at multiple dilutions, and represents the combined average of 6 separate samples. ASCs cultured as adherent monolayers in D0 medium did not survive the 10-day culture conditions. The ordinate represents the amount of growth factor (GF) per cell. Each bar of the bar graph is labeled below with the growth factor being measured.
Figure 10:
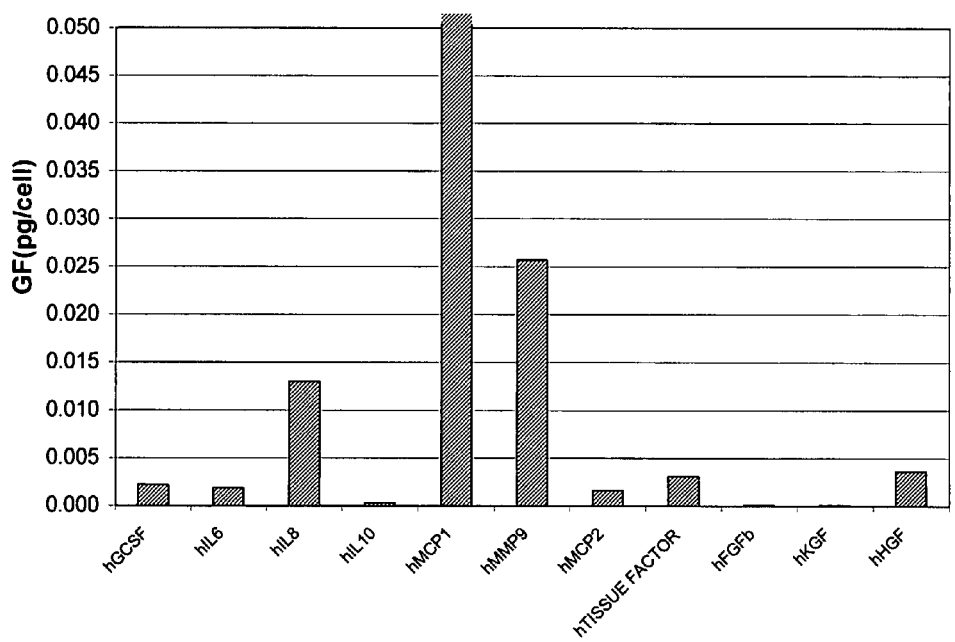
FIG. 10 is a graphic illustration of growth factor production by suspension cultured human ASC SNiMs maintained in serum-free, growth factor enriched medium (Day 10). After hanging drop culture for 2 days, human ASC SNiMs were placed into suspension culture and maintained for 10 days in 1:10 AR8 medium. Media was replaced on days 3, 6 and 10. On day 10, supernatant was collected for ELISA analysis and SNiMs were dissociated to determine cell numbers. Each growth factor (hGCSF, hIL6, hIL8, hIL10 hMCP1, hMMP9, hMCP2, hTissue Factor, hFGFb, hKGF, and hHGF) was measured in duplicate at multiple dilutions, and the values represent the combined average of 6 separate samples. ASCs cultured as adherent monolayers in similar conditions did not thrive during the 10 day culture period. The ordinate represents the amount of growth factor per cell and each bar is labeled with the growth factor being measured.
Figure 11:
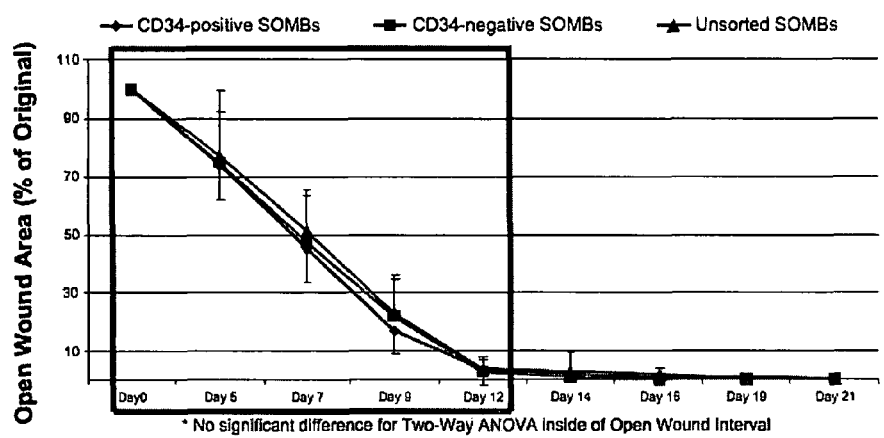
FIG. 11 is a graphic illustration of an experiment demonstrating that sorting ASCs based on CD34 has no effect on healing rate. The ordinate represents open wound area (as % of original size of wound) and the abscissa represents time in days. The three Groups are CD34-positive SOMBs (♦), CD34-negative SOMBs (■), and unsorted SOMBs (▲).

ASC-SOM-Bs (SNiMs) can be cultured successfully in suspension (i.e., floating) culture using ultra low attachment (ULA) culture ware. They can survive for at least 6 months in suspension culture (the longest time point tested), based on microscopic appearance, H&E histology, and their ability to spawn new cells when subsequently placed into adherent culture. Even ASC-SOM-Bs (SNiMs) grown in DMEM/F12 without any additives (D-0) remain viable for as long as one month-maintaining a compact architecture, exhibiting persistent DiI fluorescence and demonstrating the ability to readily attach to tissue culture plastic and spawn new cells that grow to monolayer confluence (data not shown). In addition, as described below, ASC-SOM-Bs (SNiMs) grown in suspension secrete detectable levels of numerous growth factors, even when maintained in D0 medium (FIGS. 8-10).

III. ASC-SOM-Bs (SNiMs) are Composed of Cells and Variable Amounts of Self-Generated Extracellular Matrix.

To determine the cellularity and cellular topography of ASC-SOM-Bs (SNiMs) in suspension, Hoechst stain was used to label nuclei. This revealed extensive and uniform cellularity on the outer surface of the ASC-SOM-Bs (SNiMs). To further evaluate the cellularity and architecture of ASC-SOM-Bs (SNiMs), some ASC-SOM-Bs (SNiMs) were fixed, sectioned, and stained with H&E, Trichrome and Safranin O. H and E staining reveals uniform cell (i.e. nuclei) distribution throughout the entire SOM-B (SNiM) cross-section, embedded within hyaline-positive matrix. Staining with Trichrome reveals the presence of extensive collagen-based ECM. To this end, ASC-SOM-Bs (SNiMs) were subjected to a variety of enzymatic and mechanical strategies in efforts to dissociate and (re)-isolate their cellular components. ASC-SOM-Bs (SNiMs) that were more than several days old were found to be exceptionally robust and durable, resisting mechanical dissociation strategies. Enzymatic compounds (collagenase, trypsin, blendzyme, etc.) produced the best dissociation, further reflecting the presence of an established extracellular matrix milieu within the ASC-SOM-B (SNiM).

IV. ASC-SOM-Bs (SNiMs) Grown in Suspension Culture Produce Numerous Growth Factors that are Relevant to Tissue Repair, Angiogenesis and Matrix Remodeling, Even Under Serum Free Conditions.

ASC-SNiMs were maintained in suspension culture in 4 different media: D-0, D-10, 1:10 AR8 and 1:10 AR8-1% HS. At various time points, culture supernatant was harvested and growth factor levels quantified using ELISA-based assays. Results indicate that ASC-SOM-Bs (SNiMs) secrete a number of different growth factors that are relevant to wound healing and tissue repair such as those related to angiogenesis (ex. VEGF, PLGF, HGF), inflammation (ex. IL-6, IL-8, G-CSF), and matrix remodeling (ex. fibronectin, MMP-2, MMP-9, and TIMP 1 and 2) (See FIGS. 8-10). Of note, ASC-SOM-Bs (SNiMs) demonstrate consistent levels of GF secretion regardless of vastly different culture mediums, in contrast to ASCs grown in monolayer culture (FIG. 8). In many cases, ASCs grown as SOM-Bs (SNiMs) also demonstrate notably higher levels of GF production when compared to ASCs grown as monolayer cultures (FIGS. 8-10). In contrast to ASCs grown as SOM-Bs (SNiMs), ASCs in monolayer culture did not survive (D0) or grow well (1:10 AR8) over the 10 day period when maintained in serum-free conditions (FIGS. 9 and 10).

For example, FIG. 8 illustrates that human hepatocyte growth factor is produced by human ASCs in culture. Equal numbers of human ASCs were plated into monolayer culture or formed in parallel into SOM-Bs (SNiMs) and placed in suspension culture (Day 0). The cells/SOM-Bs (SNiMs) were cultured in one of four mediums: DMEM/F12 with NO other additives except antibiotics (D0); DMEM/F12 with 10% FBS (D10); chemically defined serum-free medium with growth factor additives (AR8(1:10)noS); and low serum medium (AR8(1:10) with 1% human serum (HS). On day 3, culture supernatant was collected and analyzed by ELISA for growth factor levels. Each sample was tested in duplicate at multiple dilutions, and represents the combined average of 6 separate samples.

FIG. 9 demonstrates that multiple growth factors are detected in the unfortified medium of ASC-SOM-Bs (SNiMs) on day 10. After hanging drop culture for 2 days, human ASC-SOM-Bs (SNiMs) were placed into suspension culture and maintained for 10 days in D0 medium (i.e., no serum, no growth factor additives). Media was replaced on days 3, 6 and 10. On day 10, supernatant was collected for ELISA analysis and SOM-Bs (SNiMs) were dissociated to determine cell numbers. Each growth factor was tested in duplicate at multiple dilutions, and results depicted represent the combined average of 6 separate samples. ASCs cultured as adherent monolayers in D0 medium did not survive the 10-day culture conditions.

FIG. 10 demonstrates growth factor production by suspension cultured human ASC-SOM-Bs (SNiMs) maintained in serum-free, growth factor enriched medium. After hanging drop culture for 2 days, human ASC-SOM-Bs (SNiMs) were placed into suspension culture and maintained for 10 days in 1:10 AR8 medium. Media was replaced on days 3, 6 and 10. On day 10, supernatant was collected for ELISA analysis and SOM-Bs (SNiMs) were dissociated to determine cell numbers. Each growth factor was tested in duplicate at multiple dilutions, and represents the combined average of 6 separate samples. ASCs cultured as adherent monolayers in similar conditions did not thrive during the 10 day culture period.

See also FIGS. 1-11.

The results of growth factor levels found when just SOM-Bs were used versus Dermagraft® were compared (See Table 2).

TABLE 2

HOW DO SOM-B GROWTH FACTOR LEVELS COMPARE TO DERMAGRAFT?

| GROWTH FACTOR | DG VALUE* | SOM-B VALUE** |
|---|---|---|
| VEGF | 1.1 NG/ML | 105 NG/ML |
| HGF | 2.6 NG/ML | 30 NG/ML |
| TGFβ1 | 500 PG/ML | 3,750 PG/ML |
| IL-6 | 1.5 NG/ML | 30 NG/ML |
| IL-8 | 50 NG/$10^6$ CELLS | 200 NG/$10^6$ CELLS |
| G-CSF | 1.4 NG/$10^6$ CELLS | ~100 NG/$10^6$ CELLS |

*VALUES GIVEN FOR 120 $MM^3$ PIECE OF DERMAGRAFT AND FREEZE-THAW; JN MANSBRIDGE ET. AL., DIABETES, OBESILTY AND METABOLISM, 1999.
**EXTRAPOLATED FROM SOM-B VOLUME: ASSUME SOM-B DIAMETER 0.5 MM, THEN SOM-B VOLUME IS $4/3\Pi (0.25)^3$ × 6 SOM-BS = 0.3925 $MM^3$; 120/0.3925 =~306; ABOVE SOM-B GF VALUES MULTIPLIED BY FACTOR OF 300.

Discussion:

The experiments described above were begun based on the observation that ASCs sometimes spontaneously form discrete cellular "clusters" or "nodules" in monolayer culture conditions, especially when grown in low-serum or serum free conditions. This suggested to us that ASCs are able to provide the necessary factors and conditions for their own survival by organizing themselves into a 'network', or niche. This hypothesis is supported by our findings that ASCs survive and remain biologically active as SOM-Bs (SNiMs), even when cultured in spartan culture conditions such as D0 medium. ASC-SOM-Bs (SNiMs) produce a number of growth factors associated with angiogenesis, matrix remodeling, inflammation, and cell growth and differentiation at varied levels when grown in suspension culture, depending on the culture media used. Interestingly, ASC-SOM-Bs (SNiMs) generally produce higher levels of growth factors than ASCs grown in monolayer culture, regardless of the culture medium. This is strikingly true when D0 medium is used, as ASCs do not survive in monolayer culture in this medium. Together, these findings suggest that ASC-SOM-Bs (SNiMs) function like a niche environment capable of sustaining the viability of the cell constituents and supporting their renewal and biological activity even in the most austere culture conditions.

The ability of ASCs to form and remain viable as SOM-Bs (SNiMs) when prepared and grown in serum free conditions has translational implications. Mesenchymal stem cells in general, and adipose stem cells in particular, hold great promise for future clinical therapies that enhance the body's natural ability to heal itself. One hurdle common to the use of these potential therapies, however, is the common practice of using fetal bovine serum (or other animal sera) in the culture media of cells intended for use in humans. The undefined and variable nature of animal sera, as well as the associated risk of introducing xenobiotic pathogens and triggering severe allergic responses in some subjects, presents an important consideration. In addition, the use of serum makes an already dynamic system even more variable, given the poorly defined composition of serum, and lot-to-lot variability. At the very least, it seems logical that human serum is more appropriate for human cells than bovine serum or other xenobiotic sources. To this end, our data demonstrate that ASCs grow readily in culture medium with 1% human serum, both as monolayers and as SOM-Bs (SNiMs) in suspension. For translational goals, 1% human serum could easily be utilized in an autologous paradigm.

ASC-SOM-Bs (SNiMs) show dramatically different growth characteristics depending on their culture environment. The most dramatic growth—in terms of overall size—is obtained when they are grown in suspension in serum-free medium containing multiple growth factors and additives (AR8). We have observed some SOM-Bs (SNiMs) that measure nearly 1 mm in diameter/length, and they routinely grow to 400-700 μm in diameter in AR8 medium. This upper size limit is largely independent of the number of cells originally used to form the SOM-B (SNiM). In other words, SOM-Bs (SNiMs) formed with 5,000 cells grow to the same general (maximal) size as SOM-Bs (SNiMs) formed with 30,000 cells. While SOM-B (SNiM) growth is related to the culture milieu, the upper limit of growth is likely determined by two primary factors: shape and diffusion distance. When SOM-Bs (SNiMs) enlarge concentrically as a spheroid shape, cells in the center are equidistant from the culture medium. In a sphere of 400 um diameter, the maximum diffusion distance would be 200 μm. This distance is traditionally thought to be too large to sustain cells by diffusion, yet H&E staining and BrdU staining demonstrate viable cells in the core of such SOM-Bs (SNiMs). In addition to cells, H&E staining also reveals the presence of extracellular matrix within the SOM-Bs (SNiMs). It is possible that matrix deposition is related to hypoxic conditions within the niche. At the same time, the deposited matrix might serve as a sink/reservoir for nutrients, growth factors and the like, helping to sustain cell viability under hypoxic conditions.

SOM-Bs (SNiMs) also grow asymmetrically in elongated shapes in suspension, serum-free conditions. This may be related to growth factor gradients, sub-specialization of cells within the niche or purely random phenomenon. Although elongated growth sometimes produces SOM-Bs (SNiMs)/structures of notable length, diffusion distances compatible with viability are maintained by limited width. The ability of ASC SOM-Bs (SNiMs) to regulate their size and organization is also reflected in aggregation studies. When multiple large SOM-Bs (SNiMs) in suspension culture are allowed to contact with each other and fuse, the resulting structure/conglomerate is extremely large. Over time, however, the SOM-B (SNiM)aggregate re-organizes its shape and dimensions to that seen with single SOM-Bs (SNiMs). This (re)organization may involve apoptosis and/or matrix remodeling and likely reflects aspect-ratio limits that are defined by effective diffusion distances. We are exploring these hypotheses in continued studies. Nevertheless, our data strongly support the concept of the ASC-SOM-B (SNiM) as a self-regulating stem cell niche.

The concept of a stem cell "population" as opposed to a stem "cell" is subtle but important. Cells do not exist in isolation in vivo, nor do they exist as 2-dimensional monolayers. From a biological/therapeutic perspective, one might argue that properties such as extended self-renewal and multilineage developmental plasticity are more appropriately studied (within the context of cell populations, rather than clonally-isolated cells) using, and characteristic of (3-D) stem cell "populations," rather than isolated, clonal cells. The study of stem cell biology using reductionist approaches presents creates a conundrum akin to the Heisenberg uncertainty principle of quantum physics. The more isolated a given cell (i.e. clonal), the more contrived the culture environment is likely to be, as cells do not normally exist in isolation. The cell(s) that is studied in this manner, therefore, may not reflect at all the identity and behavior of the same cell in situ/in vivo. A systems-based approach to stem cell biology embraces the complexity and reality of in vivo conditions, in contrast to traditional reductionist approaches that tend to 'artificially' simplify them. Although the use of systems-based models may seemingly involve more complexity, this does not necessarily mean they are uncontrolled or undefined. On the contrary, in the case of ASC-SOM-Bs (SNiMs), for instance, the behaviors and interactions of cells within a 3-D niche can be studied using defined, well-controlled culture conditions, without unknowns associated with the use of serum.

SOM-Bs (SNiMs) differentially express a large number of genes compared to the same cells grown as traditional monolayer culture (data not shown). SOM-Bs (SNiMs) make higher levels of growth factors compared to traditional monolayer culture techniques. The biology of SOM-Bs (SNiMs) seems to be more reproducible and consistent than cells grown as monolayer culture. Additionally, SOM-Bs (SNiMs) seem to heal diabetic wounds better than same cells grown as monolayer culture and delivered as suspension cells. These results suggest that the methods for growing the cells may be as important as the cells used. Therefore, the SNiM concept of a cell niche provides advantages and benefits for science and therapeutic efficacy.

Example 3

Diabetic Wound Healing Response to CD-34-Sorted and Unsorted Adipose-derived Stromal Cells Delivered as Self Organizing Mesenchoid Bodies Methods:

Human ASCs were isolated from an elective lipectomy specimen using well-documented methods. Cells were cultured on plastic and sorted at P=3 for expression of CD-34. CD-34-positive, CD-34-negative, and unsorted ASCs were then grown as SOMBs (25,000 ASCs/SOMB) in suspension culture for 8 days in serum free medium. On Day 0, a single 1 cm diameter full thickness excisional cutaneous wound was made on the back of homozygous diabetic null mice. Each wound was randomly treated in a blinded fashion on post-wounding day 1 with 5 SOMBs delivered topically in ~20 µl PBS under a Tegaderm dressing. The resulting ASC treatment groups consisted of: CD-34-positive ASC SOMBs (N=7), CD-34-negative ASC SOMBs (N=9), and unsorted ASC SOMBs (N=4). Digital images were taken of each wound every 2 or 3 days until Day 21 and open wound area, expressed as a percentage of initial wound area, was quantified using ImageJ analysis software.

Results:

Wound areas in all three experimental groups were statistically similar to one another at each timepoint, suggesting that prospective sorting based on CD-34 expression had no impact on the ASCs' ability to influence wound healing. In addition, healing rates in ASC SOMB-treated wounds were statistically similar to those in diabetic mice treated with vehicle control for the first week after wounding. However, by day 9, all diabetic wounds treated with ASC SOMBs were significantly smaller than those in diabetic mice receiving vehicle control and statistically similar to wild type non-diabetic mice (from a historical dataset). (See FIG. 11)

Conclusion:

The administration of ASCs as SOMBs accelerates the wound healing process in diabetic mice compared to those receiving no ASC treatment. However, prospective ASC enrichment on the basis of CD-34 expression did not enhance this therapeutic effect (See FIGS. 1-11 and Tables 1 and 2).

The disclosures of each and every patent, patent application, and publication cited herein are hereby incorporated by reference herein in their entirety. One of skill in the art will appreciate that the superiority of the compositions and methods of the invention relative to the compositions and methods of the prior art are unrelated to the physiological accuracy of the theory explaining the superior results.

Headings are included herein for reference and to aid in locating certain sections. These headings are not intended to limit the scope of the concepts described therein under, and these concepts may have applicability in other sections throughout the entire specification.

Other methods which were used but not described herein are well known and within the competence of one of ordinary skill in the art of clinical, chemical, cellular, histochemical, biochemical, molecular biology, microbiology and recombinant DNA techniques.

The description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Accordingly, the present invention is not intended to be limited to the embodiments shown herein but is to be accorded the widest scope consistent with the principles and novel features disclosed herein.

What is claimed is:

1. A method of treating a cutaneous wound comprising
   (i) culturing human adipose tissue derived stem cells that are depleted of $CD45^+$ cells, wherein the adipose tissue derived stem cells are induced to form at least one self-organizing mesenchymal blastema (SOMB); and
   (ii) topically or directly administering to the cutaneous wound in a human subject in need thereof a therapeutically effective amount of the SOMB obtained from step (i) in combination with one or more therapeutic agents selected from the group consisting of Granulocyte-Colony Stimulating Factor (GCSF), Interleukin-6 (IL6), Interleukin-8 (IL8), Interleukin-10 (IL10), Monocyte Chemotactic Protein-1 (MCP1), Monocyte Chemotactic Protein-2 (MCP2), Keratinocyte Growth Factor (KGF), Placental Growth Factor (PLGF), Matrix Metalloproteinase-1 (MMP1), Matrix Metalloproteinase-9 (MMP9), Tissue Inhibitor Metallopeptidase 1 (TIMP1), and Tissue Inhibitor Metallopeptidase 2 (TIMP2) so as to treat said cutaneous wound, wherein said cutaneous wound is associated with diabetes and said adipose tissue is obtained from said subject.

2. The method of claim 1, wherein said composition further comprises a delivery vehicle.

3. The method of claim 1, wherein said wound is a diabetic skin ulcer.

4. The method of claim 1, wherein said self-organizing mesenchymal blastema further comprises at least one cell type other than an adipose tissue-derived stem cell or is administered with at least one cell type other than an adipose tissue-derived stem cell.

5. The method of claim 1, wherein said at least one self-organizing mesenchymal blastema comprises at least one cell which secretes at least one factor capable of modulating the activity or function of other cells which are not substituents of the at least one self-organizing mesenchymal blastema.

6. The method of claim 1, further wherein a medical dressing is applied to the wound.

7. The method of claim 6, wherein said dressing is applied before the cells are administered.

8. The method of claim 1, wherein said at least one SOMB is formed by culturing said human adipose tissue derived stem cells in hanging droplets.

9. The method of claim 8, wherein said at least one SOMB further comprises at least one cell type other than an adipose tissue-derived stem cell or is administered with at least one cell type other than an adipose tissue-derived stem cell.

* * * * *